United States Patent
Scheidt et al.

(10) Patent No.: US 11,840,514 B2
(45) Date of Patent: Dec. 12, 2023

(54) CATALYSTS AND METHODS FOR ENANTIOSELECTIVE CONJUGATE ADDITION OF AMINES TO UNSATURATED ELECTROPHILES

(71) Applicant: Northwestern University, Evanston, IL (US)

(72) Inventors: Karl A. Scheidt, Evanston, IL (US); Brice Uno, Highland Park, IL (US)

(73) Assignee: Northwestern University, Evanston, IL (US)

( * ) Notice: Subject to any disclaimer, the term of this patent is extended or adjusted under 35 U.S.C. 154(b) by 434 days.

(21) Appl. No.: 17/027,687

(22) Filed: Sep. 21, 2020

(65) Prior Publication Data

US 2021/0002221 A1  Jan. 7, 2021

Related U.S. Application Data

(62) Division of application No. 16/448,821, filed on Jun. 21, 2019, now Pat. No. 10,781,172.

(60) Provisional application No. 62/687,912, filed on Jun. 21, 2018.

(51) Int. Cl.
| | | |
|---|---|---|
| *C07D 207/416* | (2006.01) | |
| *B01J 31/18* | (2006.01) | |
| *C07D 405/12* | (2006.01) | |
| *C07D 401/04* | (2006.01) | |

(52) U.S. Cl.
CPC ........ *C07D 207/416* (2013.01); *B01J 31/185* (2013.01); *C07D 401/04* (2013.01); *C07D 405/12* (2013.01); *B01J 2231/348* (2013.01); *B01J 2531/23* (2013.01)

(58) Field of Classification Search
None
See application file for complete search history.

(56) References Cited

U.S. PATENT DOCUMENTS

| | | |
|---|---|---|
| 7,851,640 B2 | 12/2010 | Scheidt |
| 8,912,341 B2 | 12/2014 | Scheidt |
| 9,309,217 B2 | 4/2016 | Scheidt |
| 9,334,297 B2 | 5/2016 | Scheidt |
| 9,527,812 B2 | 12/2016 | Scheidt |
| 9,624,190 B2 | 4/2017 | Scheidt |
| 9,643,947 B2 | 5/2017 | Scheidt |
| 9,840,487 B2 | 12/2017 | Scheidt |
| 9,981,968 B2 | 5/2018 | Schiltz |
| 10,308,624 B2 | 6/2019 | Scheidt |
| 10,323,039 B2 | 6/2019 | Scheidt |
| 10,654,865 B2 | 5/2020 | Scheidt |
| 10,781,172 B2 * | 9/2020 | Scheidt .............. C07D 207/416 |
| 2002/0004513 A1 | 1/2002 | Andersson |
| 2006/0019998 A1 | 1/2006 | Wager |
| 2014/0206886 A1 | 7/2014 | Scheidt |
| 2015/0065703 A1 | 3/2015 | Scheidt |
| 2015/0191452 A1 | 7/2015 | King |
| 2016/0002252 A1 | 1/2016 | Schiltz |
| 2019/0276458 A1 | 9/2019 | Schiltz |
| 2020/0181106 A1 | 6/2020 | Scheidt |
| 2020/0399241 A1 | 12/2020 | Scheidt |
| 2021/0009547 A1 | 1/2021 | Scheidt |
| 2021/0009603 A1 | 1/2021 | Scheidt |

FOREIGN PATENT DOCUMENTS

WO  2004022536 A1  3/2004

OTHER PUBLICATIONS

Uno et al, Chemical Science, vol. 9, No. 6, pp. 1634-1639, Jan. 10, 2018.*
Galvis et al, Organic & Biomolecular Chemistry, vol. 11, No. 3, pp. 407-411 (Year: 2013).*
Ashraf et al, Tetrahedron, vol. 48, No. 32, pp. 6747-6756 (Year: 1992).*
Zubkov et al, Organic Biomolecular Chemistry, vol. 15, pp. 6447-6450 (Year: 2017).*
Ashton, P. R., et al. "Using polarization effects to alter chemical reactivity: A simple host which enhances amine nucleophilicity." Organic letters 2.10 (2000): 1365-1368.
Begouin, J.-M., et al. "Calcium-Based Lewis Acid Catalysts." Chemistry—A European Journal 19.25 (2013): 8030-8041.
Bellavista, T., et al. "Asymmetric Hydroazidation of Nitroalkenes Promoted by a Secondary Amine-Thiourea Catalyst." Advanced Synthesis & Catalysis 357.14-15 (2015): 3365-3373.
Bi, Y., et al. "Chemoselective, accelerated and stereoselective aza-Michael addition of amines to N-phenylmaleimide by using TMEDA based receptors." Tetrahedron: Asymmetry 15.23 (2004): 3703-3706.
Bouzard, D., et al. "Fluoronaphthyridines as antibacterial agents. 4. Synthesis and structure-activity relationships of 5-substituted 6-fluoro-7-(cycloalkylamino)-1, 4-dihydro-4-oxo-1, 8-naphthyridine-3-carboxylic acids." Journal of medicinal chemistry 35.3 (1992): 518-525.
Chen, Y. K., et al. "Enantioselective organocatalytic amine conjugate addition." Journal of the American Chemical Society 128.29 (2006): 9328-9329.
Chiyoda, K., et al. "Total syntheses of all the amathaspiramides." Angewandte Chemie International Edition 51.10 (2012): 2505-2508.
Davies, J., et al. "The first calcium-catalysed Nazarov cyclisation." Chemical Communications 50.96 (2014): 15171-15174.

(Continued)

*Primary Examiner* — Zinna Northington Davis
(74) *Attorney, Agent, or Firm* — QUARLES & BRADY LLP

(57) ABSTRACT

Disclosed are complexes and methods of using the complexes as catalysts for addition of amines to unsaturated electrophiles, as well as novel compounds produced by the disclosed complexes and methods. The disclosed methods may utilize the disclosed complexes as catalysts for adding unprotected primary amines and secondary amines to unsaturated electrophiles in an enantioselective manner to produce novel compounds which may include amino substituted succinimide compounds.

7 Claims, 7 Drawing Sheets

(56) References Cited

OTHER PUBLICATIONS

Davies, S. G., et al. "The conjugate addition of enantiomerically pure lithium amides as chiral ammonia equivalents part II: 2005-2011." Tetrahedron: Asymmetry 23.15-16 (2012): 1111-1153.

Davies, S. G., et al. "The conjugate addition of enantiomerically pure lithium amides as homochiral ammonia equivalents: scope, limitations and synthetic applications." Tetrahedron: Asymmetry 16.17 (2005): 2833-2891.

Didier, D., et al. "Samarium Iodobinaphtholate: An Efficient Catalyst for Enantioselective Aza-Michael Additions of O-Benzylhydroxylamine to N-Alkenoyloxazolidinones." European Journal of Organic Chemistry 2011.14 (2011): 2678-2684.

Dinér, P, et al. "Enantioselective Organocatalytic Conjugate Addition of N Heterocycles to α, β-Unsaturated Aldehydes." Angewandte Chemie 119.12 (2007): 2029-2033.

Dulin, C. C., et al. "Calcium-catalyzed Friedel-Crafts addition of 1-methylindole to activated cyclopropanes." Tetrahedron letters 55.38 (2014): 5280-5282.

Enders, D. et al. "Enantioselective synthesis of 3H-pyrrolo [1, 2-a] indole-2-carbaldehydes via an organocatalytic domino aza-Michael/aldol condensation reaction." Synthesis 2009.24 (2009): 4119-4124.

Enders, D. et al. "Organocatalytic asymmetric aza-Michael additions." Chemistry—A European Journal 15.42 (2009): 11058-11076.

Estermann, H. et al. "Diastereoselektive Alkylierung von 3-Aminobutansäure in der 2-Stellung." Helvetica chimica acta 71.7 (1988): 1824-1839.

Fadini, L., et al. "Ni (II) Complexes containing chiral tridentate phosphines as new catalysts for the hydroamination of activated olefins." Chemical Communications 1 (2003): 30-31.

Guerin, D. J. et al. "Amine-catalyzed addition of azide ion to α, β-unsaturated carbonyl compounds." Organic letters 1.7 (1999): 1107-1109.

Guerin, D. J. et al. "Asymmetric Azidation—Cycloaddition with Open-Chain Peptide-Based Catalysts. A Sequential Enantioselective Route to Triazoles." Journal of the American Chemical Society 124.10 (2002): 2134-2136.

Hamashima, Y., et al. "Amine-salt-controlled, catalytic asymmetric conjugate addition of various amines and asymmetric protonation." Organic letters 6.11 (2004): 1861-1864.

Hatano, M., et al. "Chiral lithium salts of phosphoric acids as Lewis acid-base conjugate catalysts for the enantioselective cyanosilylation of ketones." Advanced Synthesis & Catalysis 350.11-12 (2008): 1776-1780.

Hatano, M., et al. "Which is the actual catalyst: chiral phosphoric Acid or chiral calcium phosphate?." Angewandte Chemie International Edition 49.22 (2010): 3823-3826.

Hoang, C. T., et al. "3-Aminopyrrolidines from α-aminoacids: total synthesis of (+)-nemonapride from D-alanine." The Journal of organic chemistry 73.3 (2008): 1162-1164.

Horstmann, T.E. et al. "Asymmetric Conjugate Addition of Azide to α,β-Unsaturated Carbonyl Compounds Catalyzed by Simple Peptides" Angewandte Chemie International Edition, 2000, 39, 3635-3638.

Ingle, G. K., et al. "Chiral Magnesium BINOL phosphate-catalyzed phosphination of imines: Access to enantioenriched α-Amino phosphine oxides." Organic letters 13.8 (2011): 2054-2057.

Isozaki, H., et al. "A new human lung adenocarcinoma cell line harboring the EML4-ALK fusion gene." Japanese journal of clinical oncology 44.10 (2014): 963-968.

Jenner, G. "Catalytic high pressure synthesis of hindered β-aminoesters." Tetrahedron letters 36.2 (1995): 233-234.

Juaristi, E., et al. "Enantioselective synthesis of. beta.-amino acids. 2. Preparation of the like stereoisomers of 2-methyl-and 2-benzyl-3-aminobutanoic acid." The Journal of Organic Chemistry 57.8 (1992): 2396-2398.

Kano, S., et al. "Formation of 2, 3-dihydro-4 (1 H)-quinolones and related compounds via Fries-type acid-catalysed rearrangement of 1-arylazetidin-2-ones." Journal of the Chemical Society, Perkin Transactions 1 (1980): 2105-2111.

Katayama, R., et al. "Mechanisms of acquired crizotinib resistance in ALK-rearranged lung cancers." Science translational medicine 4.120 (2012): 120ra17-120ra17.

Katayama, R., et al. "Therapeutic strategies to overcome crizotinib resistance in non-small cell lung cancers harboring the fusion oncogene EML4-ALK." Proceedings of the National Academy of Sciences 108.18 (2011): 7535-7540.

Kawatsura, M. et al. "Transition metal-catalyzed addition of amines to acrylic acid derivatives. A high-throughput method for evaluating hydroamination of primary and secondary alkylamines." Organometallics 20.10 (2001): 1960-1964.

Kinas, R, et al. "Synthesis and absolute configuration of the optically active forms of 2-[bis (2-chloroethyl) amino]-4-methyltetrahydro-2H-1, 3, 2-oxazaphosphorine 2-oxide (4-methylcyclophosphamide)." The Journal of organic chemistry 42.9 (1977): 1650-1652.

Kobayashi, S., et al. "Alkaline earth metal catalysts for asymmetric reactions." Accounts of chemical research 44.1 (2010): 58-71.

Lalli, C., et al. "Chiral Calcium-BINOL Phosphate Catalyzed Diastereo- and Enantioselective Synthesis of syn-1, 2-Disubstituted 1, 2-Diamines: Scope and Mechanistic Studies." Chemistry—A European Journal 21.4 (2015): 1704-1712.

Lebœuf, D. et al. "Calcium (II)-catalyzed aza-Piancatelli reaction." Organic letters 16.24 (2014): 6464-6467.

Lee, A. et al. "A Cooperative N-Heterocyclic Carbene/Chiral Phosphate Catalysis System for Allenolate Annulations." Angewandte Chemie International Edition 53.29 (2014): 7594-7598.

Li, G., et al. "An asymmetric Diels-Alder reaction catalyzed by chiral phosphate magnesium complexes: highly enantioselective synthesis of chiral spirooxindoles." Angewandte Chemie International Edition 52.17 (2013): 4628-4632.

Li, W., et al. "Asymmetric Construction of 2, 3-Dihydroisoxazoles via an Organocatalytic Formal [3+ 2] Cycloaddition of Enynes with N-Hydroxylamines." Organic letters 18.16 (2016): 3972-3975.

Liang, T., et al. "Chiral metal phosphate catalysis: highly asymmetric hetero-Diels-Alder reactions." Chemical Communications 50.91 (2014): 14187-14190.

Liu, J., et al. "Selective Palladium-Catalyzed Aminocarbonylation of Olefins to Branched Amides." Angewandte Chemie International Edition 55.43 (2016): 13544-13548.

Liu, M., et al. "Recent advances in the stereoselective synthesis of β-amino acids." Tetrahedron 40.58 (2002): 7991-8035.

Lv, J., et al. "Organocatalytic Enantioselective aza-Michael Additions of N-Heterocycles to α, ß-Unsaturated Enones." European Journal of Organic Chemistry 2010.11 (2010): 2073-2083.

Meyer, V. J., et al. "Calcium-Catalyzed Cycloisomerization of Enynes." Advanced Synthesis & Catalysis 355.10 (2013): 1943-1947.

Myers, J. K., et al. "Asymmetric synthesis of β-amino acid derivatives via catalytic conjugate addition of hydrazoic acid to unsaturated imides." Journal of the American Chemical Society 121.38 (1999): 8959-8960.

Pangborn, A. B., et al. "Safe and convenient procedure for solvent purification." Organometallics 15.5 (1996): 1518-1520.

Parmar, D., et al. "Complete field guide to asymmetric BINOL-phosphate derived Brønsted acid and metal catalysis: history and classification by mode of activation; Brønsted acidity, hydrogen bonding, ion pairing, and metal phosphates." Chemical reviews 114.18 (2014): 9047-9153.

Phillips, E. M., et al. "N-heterocyclic carbene-catalyzed conjugate additions of alcohols." Journal of the American Chemical Society 132.38 (2010): 13179-13181.

Phua, P. H., et al. "Enabling Ligand Screening for Palladium-Catalysed Enantioselective Aza-Michael Addition Reactions." Advanced Synthesis & Catalysis 348.4-5 (2006): 587-592.

Rueping, M. et al. "Chiral Brønsted Acids and Their Calcium Salts in Catalytic Asymmetric Mannich Reactions of Cyclic 1, 3-Diketones." Synlett 2011.03 (2011): 323-326.

Rueping, M., et al. "Asymmetric Calcium Catalysis: Highly Enantioselective Carbonyl-Ene and Friedel-Crafts Reactions for the Synthesis of Quaternary α-Hydroxy Esters Bearing a Trifluoromethyl Group." Chemistry—An Asian Journal 7.6 (2012): 1195-1198.

(56) References Cited

OTHER PUBLICATIONS

Rueping, M., et al. "Synthesis and Structural Aspects of N-Triflylphosphoramides and Their Calcium Salts-Highly Acidic and Effective Brønsted Acids." Chemistry—A European Journal 16.44 (2010): 13116-13126.

Shimizu, S., et al. "Calcium-catalyzed asymmetric synthesis of 3-tetrasubstituted oxindoles: efficient construction of adjacent quaternary and tertiary chiral centers." Organic letters 17.8 (2015): 2006-2009.

Sibi, M. P., et al. "Chiral Lewis acid catalysis in conjugate additions of o-benzylhydroxylamine to unsaturated amides. Enantioselective synthesis of β-amino acid precursors." Journal of the American Chemical Society 120.26 (1998): 6615-6616.

Sundararajan, G., et al. "A new polymer-anchored chiral catalyst for asymmetric Michael addition reactions." Organic letters 3.3 (2001): 389-392.

Taylor, M. S., et al. "Highly enantioselective conjugate additions to α, β-unsaturated ketones catalyzed by a (Salen) Al complex." Journal of the American Chemical Society 127.4 (2005): 1313-1317.

Thompson, S. K., et al. "Rational design of orally-active, pyrrolidine-based progesterone receptor partial agonists." Bioorganic & medicinal chemistry letters 19.16 (2009): 4777-4780.

Uraguchi, D. et al. "Chiral arylaminophosphonium barfates as a new class of charged Brønsted acid for the enantioselective activation of nonionic lewis bases." Journal of the American Chemical Society 131.21 (2009): 7242-7243.

Wang, J., et al. "Enantioselective organocatalytic Michael addition reactions between N-heterocycles and nitroolefins." Organic letters 8.7 (2006): 1391-1394.

Wang, L. et al. "Asymmetric Neutral Amination of Nitroolefins Catalyzed by Chiral Bifunctional Ammonium Salts in Water-Rich Biphasic Solvent." Angewandte Chemie International Edition 50.23 (2011): 5327-5330.

Wang, L. et al. "Highly Enantioselective Aza-Michael Reaction between Alkyl Amines and β-Trifluoromethyl β-Aryl Nitroolefins." Angewandte Chemie International Edition 54.51 (2015): 15414-15418.

Washburn, D. G., et al. "Discovery of orally active, pyrrolidinone-based progesterone receptor agonists." Bioorganic & medicinal chemistry letters 19.16 (2009): 4664-4668.

Weiß, M., et al. "Asymmetric addition of a nitrogen nucleophile to an enoate in the presence of a chiral phase-transfer catalyst: A novel approach toward enantiomerically enriched protected β-amino acids." Heteroatom Chemistry 23.2 (2012): 202-209.

Wilkins, L. C., et al. "Enantioselective main group catalysis: Modern catalysts for organic transformations." Coordination Chemistry Reviews 324 (2016): 123-139.

Xu, L-W, et al. "A Catalytic Enantioselective Aza-Michael Reaction: Novel Protocols for Asymmetric Synthesis of β-Amino Carbonyl Compounds." European journal of organic chemistry 2005.4 (2005): 633-639.

Yamagiwa, N. et al. "Heterobimetallic catalysis in asymmetric 1, 4-addition of O-alkylhydroxylamine to enones." Journal of the American Chemical Society 125.52 (2003): 16178-16179.

Yang, H.-M., et al. "Silicon-based Lewis acid assisted cinchona alkaloid catalysis: Highly enantioselective aza-Michael reaction under solvent-free conditions." Organic letters 13.24 (2011): 6508-6511.

Zhang, Y. J., et al. "In silico design and synthesis of piperazine-1-pyrrolidine-2, 5-dione scaffold-based novel malic enzyme inhibitors." Bioorganic & medicinal chemistry letters 16.3 (2006): 525-528.

Zhang, Z. et al. "Highly Enantioselective Catalytic Benzoyloxylation of 3-Aryloxindoles Using Chiral VAPOL Calcium Phosphate." Angewandte Chemie International Edition 50.5 (2011): 1135-1138.

Zheng, W., et al. "Chiral calcium VAPOL phosphate mediated asymmetric chlorination and Michael reactions of 3-substituted oxindoles." Journal of the American Chemical Society 133.10 (2011): 3339-3341.

Aikawa, K. et al. "Axial Chirality Control of Gold (biphep) Complexes by Chiral Anions: Application to Asymmetric Catalysis." Angewandte Chemie International Edition 48.33 (2009): 6073-6077.

Lv, J., et al. "Asymmetric Binary Acid Catalysis: A Regioselectivity Switch between Enantioselective 1, 2-and 1, 4-Addition through Different Counteranions of In III." Angewandte Chemie International Edition 29.50 (2011): 6610-6614.

\* cited by examiner

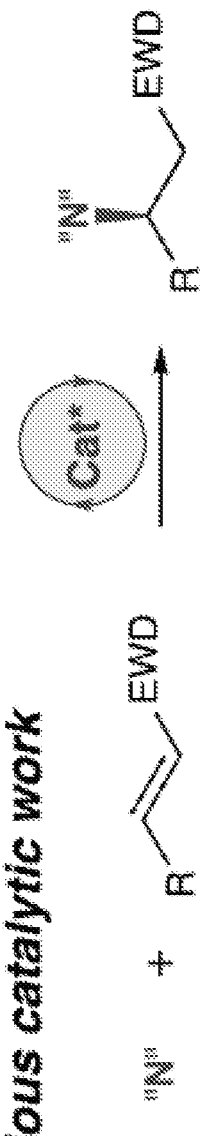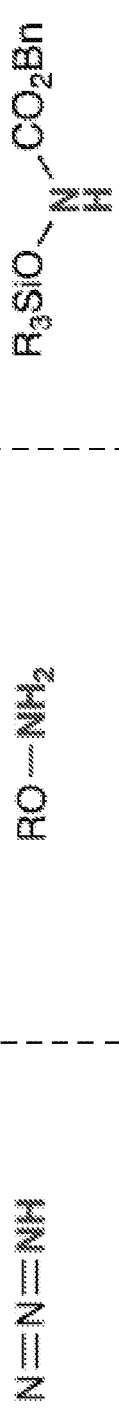
Figure 1 (continued) (prior art)

CATALYSTS AND METHODS FOR ENANTIOSELECTIVE CONJUGATE ADDITION OF AMINES TO UNSATURATED ELECTROPHILES

CROSS-REFERENCE TO RELATED PATENT APPLICATIONS

The present application claims the benefit of priority under 35 U.S.C. § 119(e) to U.S. Provisional Application No. 62/687,912 filed on Jun. 21, 2018, the content of which is incorporated herein by reference in its entirety.

BACKGROUND

The field of the invention relates to catalyzed methods for enantioselective conjugate addition of alkyl amines to unsaturated electrophiles. In particular, the field of the invention relates to catalyzed methods for enantioselective conjugate addition of unprotected alkyl amines to α,β-unsaturated electrophiles such as substituted maleimides to obtain chiral aminosuccinimide products.

Chiral amines are a ubiquitous motif in pharmaceuticals and natural products. The conjugate addition of amine nucleophiles to various α,β-unsaturated systems is a well-established transform to access the corresponding β-amino carbonyl products.[2] However, catalytic enantioselective methods for the construction of C—N bonds directly from amines remain a current challenge in synthetic organic chemistry.

Here, the inventors disclose a direct, enantioselective chiral calcium(II)•phosphate complex (Ca[CPA]$_2$)-catalyzed conjugate addition of unprotected alkyl amines to maleimides. This mild catalytic system represents a significant advance towards a general, convergent asymmetric amination of α,β-unsaturated electrophiles, providing medicinally relevant chiral aminosuccinimide products in high yields and enantioselectivities. Furthermore, the catalyst can be reused directly from a previously chromatographed reaction while maintaining both high yield and selectivity.

SUMMARY

Disclosed are complexes and methods of using the complexes as catalysts for addition of amines to unsaturated electrophiles, as well as novel compounds produced by the disclosed complexes and methods. The disclosed methods may utilize the disclosed complexes as catalysts for adding unprotected primary amines and secondary amines to unsaturated electrophiles in an enantioselective manner to produce novel compounds which may include amino substituted succinimide compounds.

The disclosed complexes for use as catalysts in the disclosed methods may have a structure described as follows:

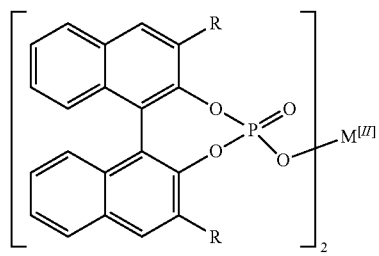

where R is aryl which optionally is substituted at one or more positions with halo, or R is aryl-substituted silicon; and M is a metal.

The disclosed complexes may form higher order complexes that optionally are hydrated. The higher order complexes may have a structure described as follows:

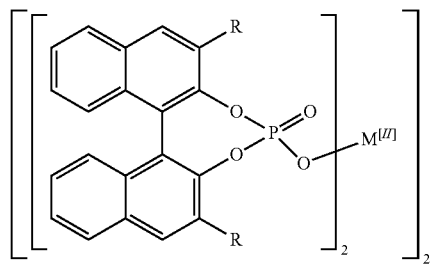

where R is aryl which optionally is substituted at one or more positions with halo, or R is aryl-substituted silicon; M is a metal; and optionally where the higher order complex is hydrated.

The disclosed complexes may be utilized as catalysts in methods for conjugating an amine to an unsaturated electrophile in an enantioselective manner, the methods comprising reacting the amine and the unsaturated electrophile in the presence of the disclosed complexes. Optionally, the disclosed complexes may be recycled after the reaction method and utilized in subsequent reaction methods. Suitable amines may include primary amines and secondary amines and suitable unsaturated electrophiles may include, but are not limited to α,β-unsaturated carbonyl compounds such as substituted maleimide compounds and derivatives thereof.

Compounds produced using the disclosed catalysts and methods may include, but are not limited to, amino substituted succinimide compounds. The disclosed novel compounds, may include, but are not limited to, compounds of a formula:

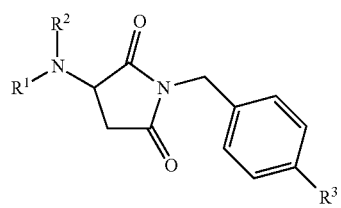

wherein

R$^1$ is alkyl, cycloalkyl, or alkenyl, or R$^1$ has a formula —CH$_2$—R$^{1'}$, wherein R$^{1'}$ is aryl, arylalkyl, or heteroaryl, which optionally is substituted at one or more positions with alkyl, halo, or alkoxy;

R$^2$ is hydrogen or alkyl; or R$^1$ and R$^2$ together form piperdinyl, piperazinyl, or morphilino, which optionally is substituted with 4-methoxyphenyl or arylalkyl; and R$^3$ is hydrogen, alkyl, alkoxy, or halo.

The compounds particularly may have a formula:

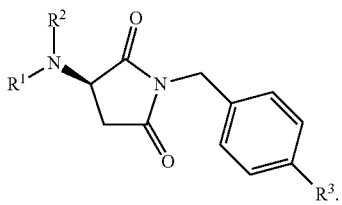

DETAILED DESCRIPTION

Figure 1:
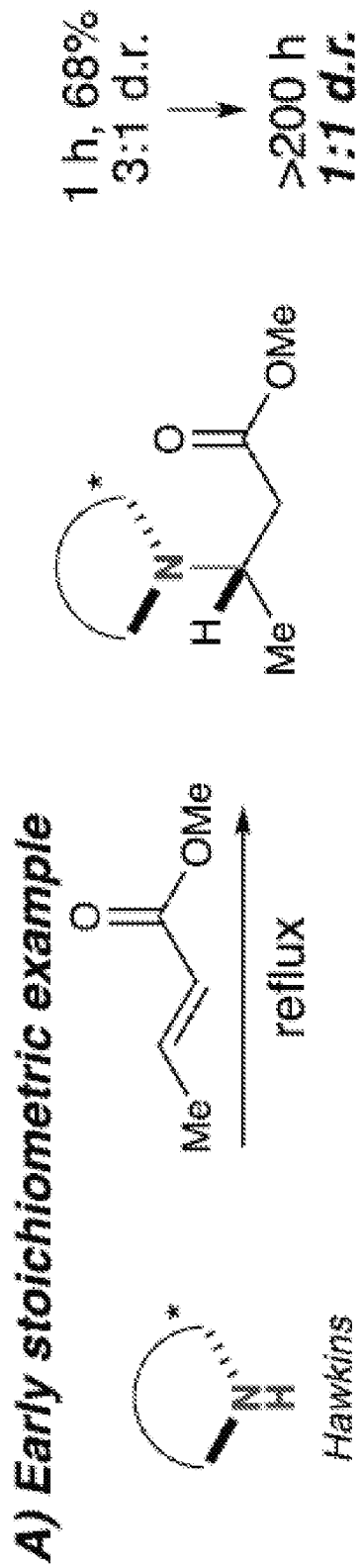
FIG. 1. Enantioselective conjugate additions of amines. A) Early stoichiometric example of the prior art. B) Previous catalytic work of the prior art. C) Illustration of the catalytic work disclosed herein. D) Biologically relevant motifs comprising substituted a pyrrolidine core, a substituted pyrrolidone core, or a partially reduced substituted succinimide core.
Figure 1:
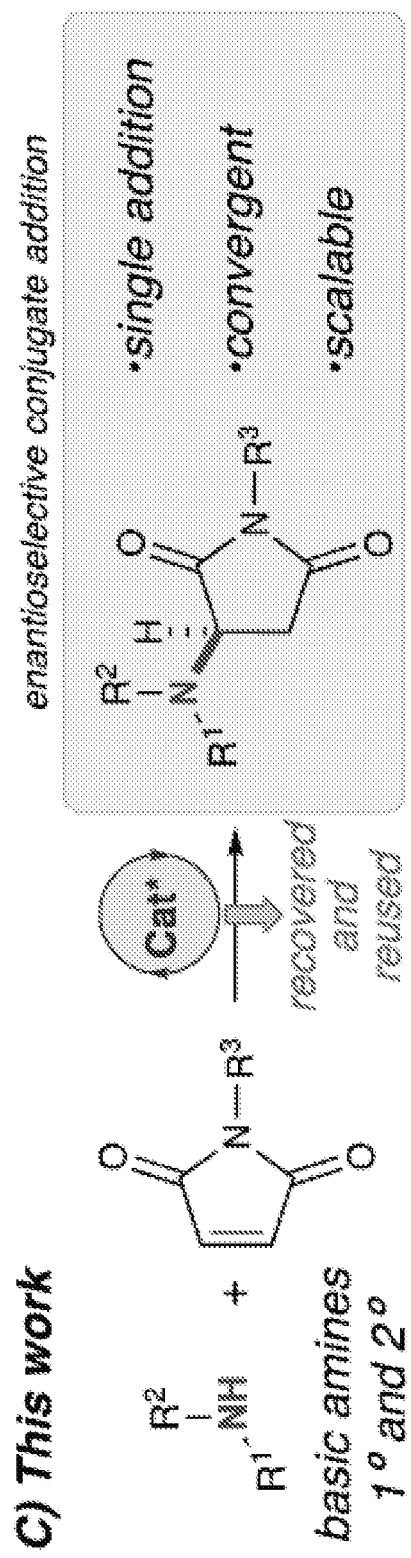
Figure 1:
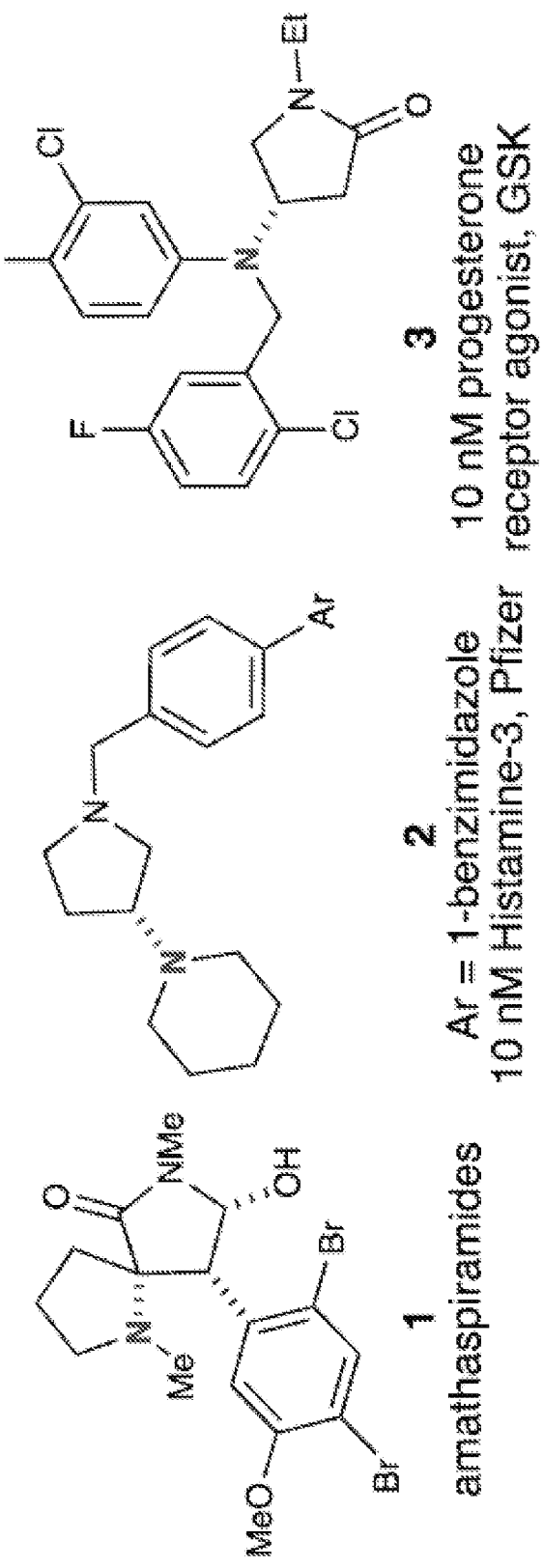

As used herein, unless otherwise specified or indicated by context, the terms "a", "an", and "the" mean "one or more." For example, "a compound" or "an inhibitor" should be interpreted to mean "one or more compounds" and "one or more inhibitors," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched C1-C6 alkyl group). Exemplary alkylene groups include, but are not limited to —CH$_2$—, —CH$_2$CH$_2$—, —CH$_2$CH$_2$CH$_2$—, —CH(CH$_3$)CH$_2$—, —CH$_2$CH(CH$_3$) CH$_2$—, —CH(CH$_2$CH$_3$)CH$_2$—, and the like.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number or ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The term "arylalkyl" refers to an alkyl group that is substituted with an aryl group. For example, term arylalkyl includes a phenylmethyl moiety otherwise referred to as a benzyl moiety.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Pharmaceutical Compositions and Formulations

The compounds disclosed herein may exhibit biological activity and may be formulated and administered as pharmaceutical compositions and, therefore, pharmaceutical compositions incorporating the compounds are considered to be embodiments of the compositions disclosed herein. For example, the disclosed compounds may exhibit biological activities similar to those of the compounds of FIG. 1 D), which have biological relevant motifs and include amathaspiramides, histamine-3 antagonists, and progesterone receptor agonists.

Such pharmaceutical compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated with the disclosed compounds' biological activity. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating one or more of the aforementioned diseases or disorders.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Catalysts and Methods for Enantioselective Conjugate Addition of Amines to Unsaturated Electrophiles Disclosed are complexes and methods of using the complexes as catalysts for addition of amines to unsaturated electrophiles, as well as novel compounds produced by the disclosed complexes and methods. The disclosed methods may utilize the disclosed complexes as catalysts for adding unprotected primary amines and secondary amines to unsaturated electrophiles in an enantioselective manner to produce novel compounds which may include amino substituted succinimide compounds.

The disclosed complexes for use as catalysts in the disclosed methods may have a structure described as follows:

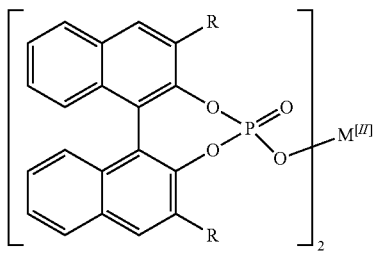

where R is aryl which optionally is substituted at one or more positions with halo, or R is aryl-substituted silicon; and M is a metal.

The disclosed complexes may form higher order complexes that optionally are hydrated. The higher order complexes may have a structure described as follows:

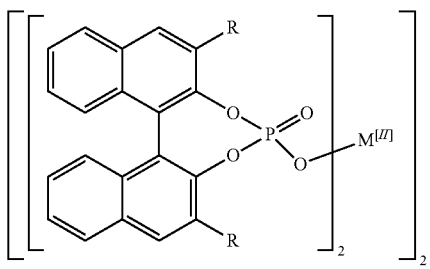

where R is aryl which optionally is substituted at one or more positions with halo, or R is aryl-substituted silicon; M is a metal; and optionally where the higher order complex is hydrated.

In some embodiments of the disclosed complexes R is selected from the group consisting of naphthalene, phenanthrene, $SiPh_3$, and $C_6F_5$. In further embodiments of the disclosed complexes R is selected from the group consisting of 1-naphthalene, 2-naphthalene, 1-phenanthrene, 2-phenanthrene, and 9-phenanthrene. In even further embodiments of the disclosed complexes R is 9-phenanthrene.

In the disclosed complexes M is a metal. In some embodiments of the disclosed complexes, M is an alkaline earth metal. In further embodiments of the disclosed complexes, M is Ca.

The disclosed complexes may be utilized as catalysts in methods for conjugating an amine to an unsaturated electrophile in an enantioselective manner, the methods comprising reacting the amine and the unsaturated electrophile in the presence of the disclosed complexes. Optionally, the disclosed complexes may be recycled after the reaction method and utilized in subsequent reaction methods.

In the disclosed reaction methods, the selected amine need not be protected prior to reacting the amine with the unsaturated electrophile. Suitable amines for the disclosed methods may include primary amines and secondary amines.

In some embodiments of the disclosed reaction methods, the amine has a formula:

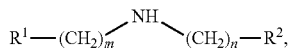

where: m is 0-6 and n is 0-6; $R^1$ and $R^2$ are selected from H, alkyl, alkylidenyl, alkylidynyl, cycloalkyl, cycloheteroalkyl, aryl, and heteroaryl, and $R^1$ and $R^2$ optionally are substituted at one or more positions with alkyl, alkoxy, or halo; or when m and n are 0, $R^1$ and $R^2$ form a 5-membered or 6-membered heterocyclic ring or $R^1$ and $R^2$ form two fused rings which may be 5-membered rings or 6-membered rings, which one ring or two fused rings optionally are saturated or unsaturated, which one ring or two rings are carbocycles or heterocycles including one or more heteroatoms (e.g., N, O, or S), which one ring or two rings optionally are substituted to include one or more non-hydrogen substituents, which non-hydrogen substituents optionally are selected from alkyl, alkyoxy, halo, haloalkyl, hydroxyl, phenyl or substituted phenyl (e.g., methoxyphenyl), and benzyl; and optionally at least one of m and n is 0, and/or and least one of $R^1$ and $R^2$ is H or alkyl.

Suitable unsaturated electrophiles for the disclosed reaction methods may include, but are not limited to α,β-unsaturated carbonyl compounds such as substituted maleimide compounds and derivatives thereof. In some embodiments, of the disclosed reaction methods, the unsaturated electrophile is a substituted maleimide compound having a formula:

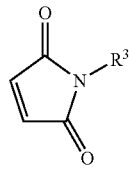

where $R^3$ is alkyl, phenyl, or benzyl, and $R^3$ is optionally substituted at one or more positions with alkyl, alkoxy, and halo.

In some embodiments of the disclosed reaction methods, the methods may be performed using molecular sieves (MS). Suitable MS may include for example 4 Å MS, which may be utilized in order to remove water from the reaction.

In some embodiments of the disclosed reaction methods, the methods may be performed at relatively low temperatures. Suitable temperatures for performing the disclosed reaction methods may include a temperature less than 4° C., –20° C., or –40° C., or a temperature within a temperature range bounded by any of these values (e.g., a temperature within a range of –20° C.-4° C.).

Compounds produced using the disclosed catalysts and methods may include, but are not limited to, amino substituted succinimide compounds. The disclosed novel compounds, may include, but are not limited to, compounds of a formula:

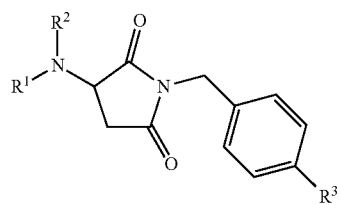

wherein
R¹ is alkyl (e.g., methyl, ethyl, propyl or isopropyl, butyl or t-butyl, pentyl, or hexyl), cycloalkyl (e.g., cyclohexyl), or alkenyl (e.g., propylenyl), or R¹ has a formula —CH₂—R¹', wherein R¹' is aryl (e.g., phenyl), arylalkyl (e.g., benzyl), or heteroaryl (e.g., furanyl), which optionally is substituted at one or more positions with alkyl (e.g. methylphenyl or tolyl such as o-tolyl, m-tolyl, or p-tolyl), halo (e.g., F, Cl, or Br), or alkoxy (e.g., methoxy or ethoxy);
R² is hydrogen or alkyl (e.g., methyl); or R¹ and R² together form piperdinyl, piperazinyl, or morphilino, which optionally is substituted with 4-methyoxyphenyl (e.g., 4-(4-methoxyphenyl)piperdinyl) or arylalkyl (e.g., N-benzyl-piperazinyl); and
R³ is hydrogen, alkyl (e.g., methyl), alkoxy (e.g., methoxy), or halo (e.g., Cl).

The compounds particularly may have a formula:

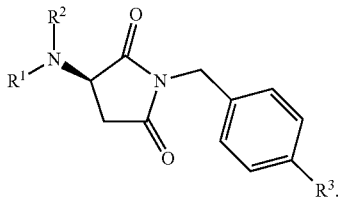

Compositions are contemplated herein in which the compositions comprise or consist of at least about 80%, 90%, 95%, 96%, 97%, 98%, or 99% of a single enantiomer of the disclosed compounds and or enantiopure compositions.

Illustrative Embodiments

The following Embodiments are illustrative and are not intended to limit the scope of the claimed subject matter.

Embodiment 1. A complex having a structure:

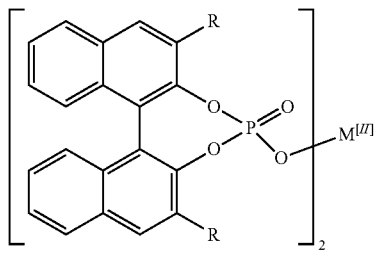

wherein
R is aryl which optionally is substituted at one or more positions with halo, or R is aryl-substituted silicon; and
M is a metal.

Embodiment 2. The complex of embodiment 1, wherein R is selected from the group consisting of naphthalene, phenanthrene, SiPh₃, and C₆F₅.

Embodiment 3. The complex of embodiment 1, wherein R is selected from the group consisting of 1-naphthalene, 2-naphthalene, 1-phenanthrene, 2-phenanthrene, and 9-phenanthrene.

Embodiment 4. The complex of embodiment 1, wherein R is 9-phenanthrene.

Embodiment 5. The complex of any of the foregoing embodiments, wherein M is an alkaline earth metal.

Embodiment 6. The complex of any of the foregoing embodiments, wherein M is Ca.

Embodiment 7. A complex having a structure:

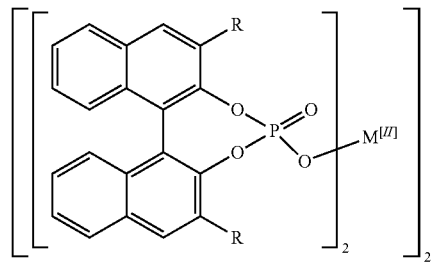

wherein
R is aryl which optionally is substituted at one or more positions with halo, or R is aryl-substituted silicon;
M is a metal; and
optionally wherein the complex is hydrated.

Embodiment 8. The complex of embodiment 7, wherein R is selected from the group consisting of naphthalene, phenanthrene, SiPh₃, and C₆F₅.

Embodiment 9. The complex of embodiment 7, wherein R is selected from the group consisting of 1-naphthalene, 2-naphthalene, 1-phenanthrene, 2-phenanthrene, and 9-phenanthrene.

Embodiment 10. The complex of embodiment 7, wherein R is 9-phenanthrene.

Embodiment 11. The complex of any of embodiments 7-10 wherein M is an alkaline earth metal.

Embodiment 12. The complex of any of embodiments 7-11, wherein M is Ca.

Embodiment 13. A method for conjugating an amine to an unsaturated electrophile, the method comprising reacting the amine and the unsaturated electrophile in the presence of the complex of any of embodiments 1-12 as a catalyst in a reaction mixture, the method optionally including recycling the complex of embodiment 1-12 for a subsequent reaction.

Embodiment 14. The method of embodiment 13, wherein the amine is unprotected.

Embodiment 15. The method of embodiment 13 or 14, wherein the amine has a formula:

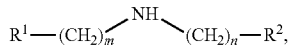

wherein m is 0-6 and n is 0-6;
wherein R¹ and R² are selected from H, alkyl, alkylidenyl, alkylidynyl, cycloalkyl, cycloheteroalkyl, aryl, and heteroaryl, and R¹ and R² optionally are substituted at one or more positions with alkyl, alkoxy, or halo; or
when m and n are 0, R¹ and R² form a 5-membered or 6-membered heterocyclic ring or R¹ and R² form two fused rings which may be 5-membered rings or 6-membered rings, which one ring or two fused rings optionally are saturated or unsaturated, which one ring or two rings are carbocycles or heterocycles including one or more heteroatoms (e.g., N, O, or S), which one ring or two rings optionally are substituted to include one or more non-hydrogen substituents, which non-hydrogen substituents optionally are selected from alkyl, alkyoxy, halo, haloalkyl, hydroxyl, phenyl or substituted phenyl (e.g., methoxyphenyl), and benzyl; and optionally at least one of m and n is 0, and/or and least one of $R^1$ and $R^2$ is H or alkyl.

Embodiment 16. The method of any of embodiments 13-15, wherein the unsaturated electrophile is an α,β-unsaturated carbonyl compound.

Embodiment 17. The method of any of embodiments 13-16, wherein the unsaturated electrophile is a maleimide compound which optionally is substituted at one or more positions with a non-hydrogen substituent.

Embodiment 18. The method of any of embodiments 13-17, wherein the unsaturated electrophile is a substituted maleimide compound having a formula:

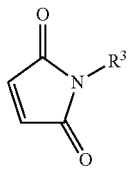

wherein $R^3$ is alkyl, phenyl, or benzyl, and $R^3$ is optionally substituted at one or more positions with alkyl, alkoxy, and halo.

Embodiment 19. The method of any of embodiments 13-18, wherein the method is performed using molecular sieves (MS), for example 4 Å MS, in order to remove water from the reaction.

Embodiment 20. The method of any of embodiments 13-19, wherein the method is performed at a temperature less than 4° C., −20° C., or −40° C., or within a temperature range bounded by any of these values (e.g., at a temperature within a range of −20° C.-4° C.).

Embodiment 21. A compound which optionally is prepared using any of the foregoing catalysts or methods, the compound optionally being an amino-substituted succinimide compound, the compound optionally being of a formula:

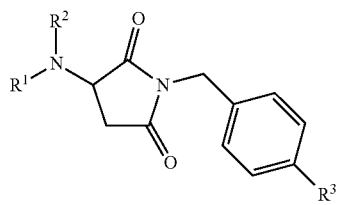

wherein
$R^1$ is alkyl (e.g., methyl, ethyl, propyl or isopropyl, butyl or t-butyl, pentyl, or hexyl), cycloalkyl (e.g., cyclohexyl), or alkenyl (e.g., propylenyl), or $R^1$ has a formula —CH$_2$—$R^{1'}$, wherein $R^{1'}$ is aryl (e.g., phenyl), arylalkyl (e.g., benzyl), or heteroaryl (e.g., furanyl), which optionally is substituted at one or more positions with alkyl (e.g. methylphenyl or tolyl such as o-tolyl, m-tolyl, or p-tolyl), halo (e.g., F, Cl, or Br), or alkoxy (e.g., methoxy or ethoxy);
$R^2$ is hydrogen or alkyl (e.g., methyl); or $R^1$ and $R^2$ together form piperdinyl, piperazinyl, or morphilino, which optionally is substituted with 4-methyoxyphenyl (e.g., 4-(4-methoxyphenyl)piperdinyl) or arylalkyl (e.g., N-benzyl-piperazinyl); and
$R^3$ is hydrogen, alkyl (e.g., methyl), alkoxy (e.g., methoxy), or halo (e.g., Cl).

Embodiment 22. The compound of embodiment 21 of a formula:

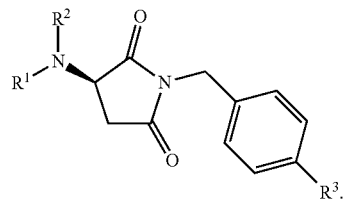

EXAMPLES

The following Examples are illustrative and are not intended to limit the scope of the claimed subject matter.

Example 1—Calcium(II)-Catalyzed Enantioselective Conjugate Additions of Amines Reference is made to the manuscript entitled "Calcium (II)-catalyzed enantioselective conjugate additions of amines," Brice E. Uno, Rachel, D. Dicken, Louis R. Redfern, Charlotte M. Stern, Greg G. Krzywicki, and Karl A. Scheidt, Chem Sci. 2018, Febr 14; 9(8): 1634-1639, the content of which is incorporated herein by reference in its entirety.

Abstract

A direct, enantioselective chiral calcium(II)·phosphate complex (Ca[CPA]$_2$)-catalyzed conjugate addition of unprotected alkyl amines to maleimides has been developed. This mild catalytic system represents a significant advance towards a general, convergent asymmetric amination of α,β-unsaturated electrophiles, providing medicinally relevant chiral aminosuccinimide products in high yields and enantioselectivities. Furthermore, the catalyst can be reused directly from a previously chromatographed reaction while maintaining both high yield and selectivity.

Introduction

Chiral amines are a ubiquitous motif in pharmaceuticals and natural products (FIG. 1).[1] The conjugate addition of amine nucleophiles to various α,β-unsaturated systems is a well-established transform to access the corresponding n-amino carbonyl products.[2] However, catalytic enantioselective methods for the construction of C—N bonds directly from amines remain a current challenge in synthetic organic chemistry. Direct conjugate additions of amines with α,β-unsaturated electrophiles have been shown to proceed at high temperatures and pressures,[3] however the reversibility of the initial attack by the amine eventually leads to racemic products. (FIG. 1A).[4] Stoichiometric homochiral lithium amides can be successfully deployed under kinetic control, achieving high yield and selectivity, however these sensitive, strongly basic reagents are further limited by the need to remove the chiral α-methylbenzyl moiety to carry the products forward to useful targets.[5] To circumvent these issues, current catalytic methods have relied upon the use of non-basic nitrogen nucleophiles as amine surrogates to avoid catalyst poisoning (FIG. 1B)[6]—a common observation when basic amines are used as reagents in the presence of chiral Lewis or Brønsted acidic catalysts.[7] To this end, numerous examples of non-basic nitrogen nucleophiles including azides,[8] hydroxylamines,[9] O-functionalized carbamates,[10] 1,2,4-triazoles,[11] indoles,[12] and anilines[13] have been strategically deployed to avoid Lewis acid complexation,[14] Brønsted acid neutralization, or unselective iminium activation.[10a] However, in all of these cases, a protected nitrogen atom is installed that requires multiple steps to elaborate further. A more convergent approach would be enabled by a direct asymmetric amination of basic primary and secondary amines without the use of protecting groups.

There appear to be only three examples of catalytic asymmetric amino-conjugate additions that have successfully employed alkyl amines.[15] In 2003, Togni briefly explored asymmetric amino-conjugate additions to activated olefins as the initial step in a catalytic asymmetric hydroamination reaction catalysed by a novel chiral Ni(II) phosphine complex.[15b] Morpholine and piperidine produced modestly enantioentriched products when reacted with methacrylonitrile (69% and 20% ee, respectively), representing a significant first example of an effective, enantioselective intermolecular hydroamination reaction employing alkyl amines. Despite this promising proof-of-concept study, general asymmetric amino-conjugate additions with unfunctionalized/masked amines remain unrealized, underscoring the fundamental challenge associated with the use of highly basic and sterically unencumbered reagents in conjunct with Lewis acidic metal catalysts. In 2015, Huang and co-workers reported an efficient, highly enantioselective conjugate addition of primary alkyl amines to activated β-aryl β-trifluoromethyl nitroolefins.[15c] Unlike most catalytic examples, their strategy uses chiral Brønsted base catalysis.[16] A major limitation to this report was the lack of secondary amines as nucleophiles. Additionally, strongly basic and cryogenic conditions were required, potentially limiting the generality of this transformation.[15c] We therefore sought mild catalytic conditions capable of providing enantioenriched amino-conjugate addition products from a general set of readily available alkyl amines with maleimides, which were chosen as as an ideal substrate for catalyst identification and optimization due to their ready availability and excellent conjugate acceptor properties (FIG. 1C). Additionally, enantioenriched aminosuccinimide products serve as an easily functionalized scaffold to generate aminolactams and aminopyrrolidines.[17] Aminosuccinimides and their derivatives are also a common motif in bioactive small molecules, pharmaceuticals, and natural products (FIG. 1D).[18] Access to these products from achiral starting materials could facilitate the rapid generation of diverse small molecule libraries aimed at probing new chemical space.

Studies and Results

We began our studies with a reaction between equimolar quantities of N-benzylmaleimide and p-tolylamine. Our primary focus was on enhancing the enantioselectivity of the title reaction (Table 1). An initial exhaustive screen of various asymmetric catalyst families including hydrogen bond donors (HBD), metal-TADDOL complexes, metal BINOL-complexes, and chiral phosphoric acids (CPA), identified CPA A-H possessing 1-napthyl substitution at the 3,3'-positions as capable of producing the title compound in modest yield and selectivity (entry 1). We investigated the role of water in the reaction and observed that the addition of 4 Å MS had a moderate but reproducible impact on selectivity (entry 2). We subsequently investigated a wide range of desiccants[9b] and found that calcium oxide had a greater than anticipated positive effect on the selectivity of the reaction (entry 3).[19] Additionally, we observed a moderate increase in e.r. over time to 80:20 e.r. (entry 4). We therefore hypothesized that calcium oxide was reacting with A-H leading to the formation of a more enantioselective calcium phosphate catalyst. Our hypothesis was informed by combining the prior elegant work of Ishihara, Antilla, and Rueping who have demonstrated the role of catalytic chiral alkali metal and alkaline earth metal-phosphate salts in various reactions.[20] Thus, we investigated two pre-formed calcium phosphate complexes (entries 5 & 6) and observed that the calcium CPA complex possessing 9-phenanthracenyl substitution on the phosphate 3,3'-positions, Ca[B]$_2$ (Table 1) facilitated the title reaction in 76% yield and 95:5 e.r. (entry 6). Strikingly, removal of 4 Å MS diminished both yield and selectivity (entry 7). After investigating selectivity as a function of temperature (entries 8 & 9), we looked at other CPA salts (entries 10-12) and determined that Ca[B]$_2$ was indeed optimal. We then compared calcium and magnesium phosphate complexes, and demonstrated again that Ca[B]$_2$ was optimal (entry 13). Increasing the concentration to 0.05 M and lowering catalyst loadings to 5 mol % increased the yield to 95% with 94:6 e.r. (entries 14 & 15).

TABLE 1

Optimization of the amino conjugate additional reaction.

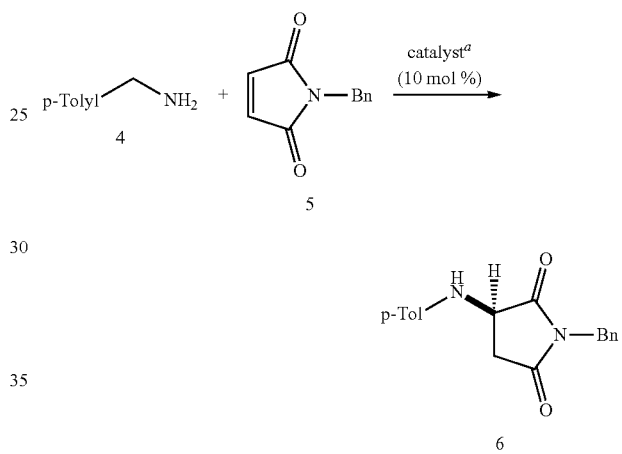

| entry | catalyst | temp (° C.) | additive | % yield | e.r. |
|---|---|---|---|---|---|
| 1. | A-H | 4 | — | 35 | 64:36 |
| 2. | A-H | 4 | 4 Å MS | 37 | 69:31 |
| 3. | A-H | 4 | CaO | 39 | 76:24 |
| 4. | A-H | 4 | CaO | 55 | 80:20[c] |
| 5. | Ca[A]$_2$ | 4 | 4 Å MS | 63 | 86;14 |
| 6. | Ca[B]$_2$ | 4 | 4 Å MS | 76 | 95:5 |
| 7. | Ca[B]$_2$ | 4 | — | 45 | 87:13 |
| 8. | Ca[B]$_2$ | −20 | 4 Å MS | 80 | 98:2 |
| 9. | Ca[B]$_2$ | −40 | 4 Å MS | 21 | 80:20 |
| 10. | Ca[C]$_2$ | −20 | 4 Å MS | 84 | 60:40 |
| 11. | Ca[D]$_2$ | −20 | 4 Å MS | 73 | 73:27 |
| 12. | Ca[E]$_2$ | −20 | 4 Å MS | 65 | 72:28 |
| 13. | Mg[B]$_2$ | −20 | 4 Å MS | 65 | 74:26 |
| 14.[d] | Ca[B]$_2$ | −20 | 4 Å MS | 94 | 94:6 |
| 15.[e] | Ca[B]$_2$ | −20 | 4 Å MS | 95 | 94:6 | catalyst structures

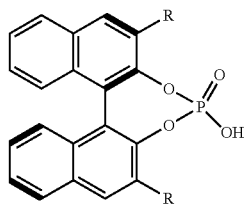

A-H; R = 1-naphthalene

TABLE 1-continued

Optimization of the amino conjugate additional reaction.

p-Tolyl-CH₂-NH₂ (4) + N-Bn maleimide (5) → p-Tol-NH-[pyrrolidine-2,5-dione]-N-Bn (6)

catalyst[a] (10 mol %)

| entry | catalyst | temp (° C.) | additive | % yield | e.r. |
|-------|----------|-------------|----------|---------|------|

M[CPA]₂

CPAs:
A, R = 1-naphthalene
B, R = 9-phenanthracene
C, R = 2-naphthalene
D, R = SiPh₃
E, R = C₆F₅

[a] 0.025 mmol scale, toluene 0.02 M, 18 h.
[b] NMR yields with 1,3,5-trimethoxybenzene as an internal standard.
[c] Time point at 48 h.
[d] toluene 0.05 M.
[e] toluene 0.05 M, 5 mol % catalyst loading of Ca[B]₂.

With the optimized conditions in hand, we next investigated the scope of the reaction with a range of aliphatic amines and maleimides (Table 2). Para-substituted primary benzylamines with a range of electron donating and withdrawing groups afforded conjugate addition products (6-11) in 93:7-94:6 e.r. and 77%-91% yield. Meta- and ortho-substituted benzyl amines afforded 12 and 13 in similar yields and selectivities. Products derived from less sterically bulky amines and linear amines were obtained with lower enantioselectivity (14-17) and moderate yields. In contrast, bulkier amines gave products 18 and 19 in high yield and selectivity. Notably, secondary cyclic amines provided conjugated products 20-24 in 93:7-97:3 e.r. These substrates would be difficult to access via other methodologies or from an enantiopure amino acid derived starting material.[21] The enantioselectivity for arylpiperidine-derived 24 uniquely improved at −40° C. and was not general for other substrates.

TABLE 2

Substrate Scope.[a]

R₁R₂NH + maleimide(N-R₃) → (R₁R₂N)-[pyrrolidine-2,5-dione]-N-R₃

Ca[B]₂ (5 mol %), toluene (0.05M), 18 h, -20° C., 4 Å MS

| X | % yield | e.r. |
|---|---------|------|
| 6  | Me  | 87 | 94:6 |
| 7  | H   | 84 | 94:6 |
| 8  | F   | 77 | 93:7 |
| 9  | Cl  | 91 | 93:7 |
| 10 | Br  | 90 | 93:7 |
| 11 | OMe | 90 | 94:6 |

12: 96%, 95:5 er (m-Me benzylamine)

13: 92%, 97:3 er (o-OEt benzylamine)

14: 49%, 88:12 er (furfurylamine)

TABLE 2-continued
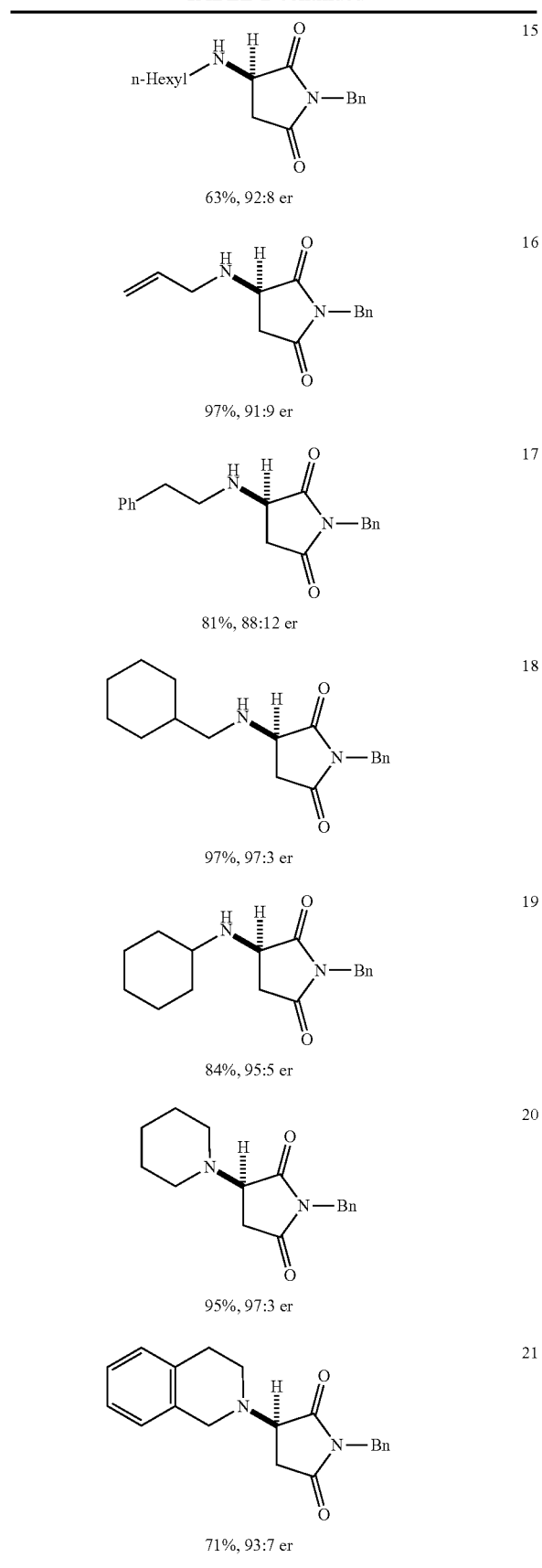
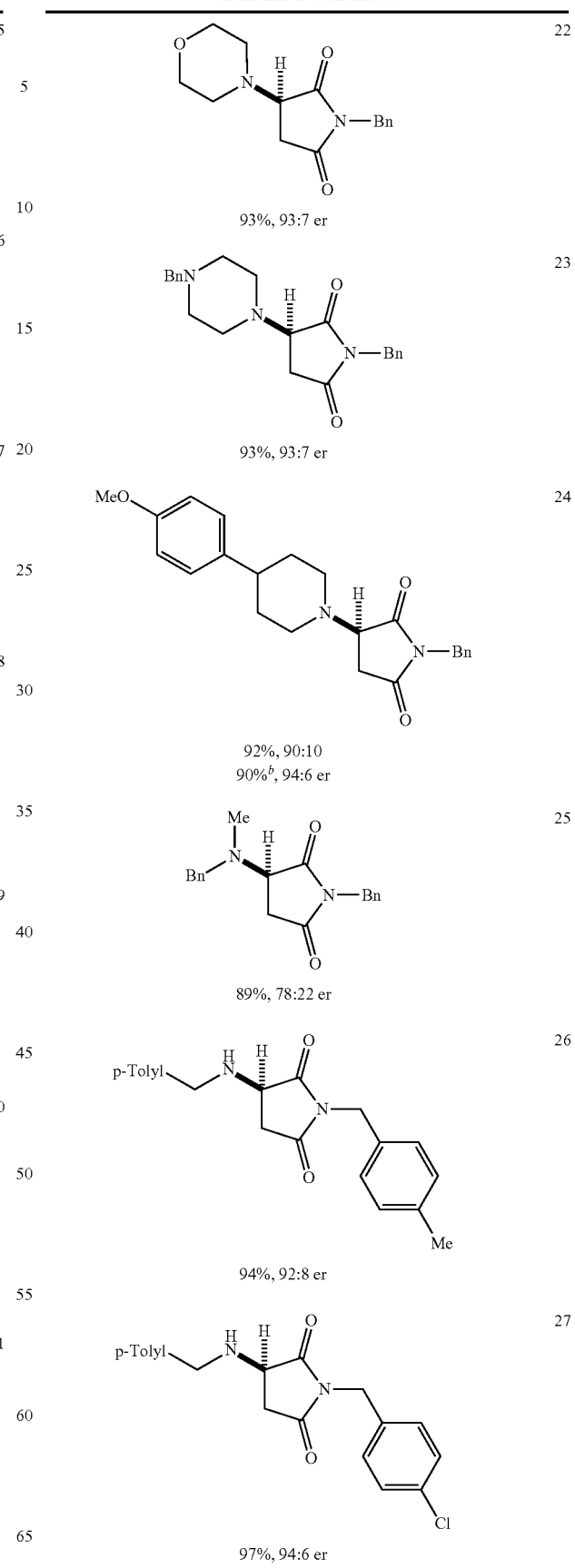

TABLE 2-continued

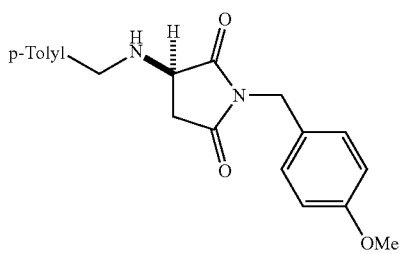

91%, 87:13 er

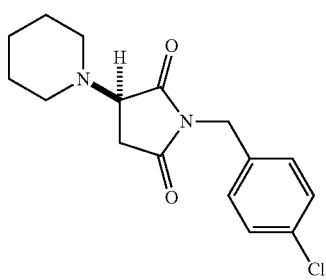

89%, 93:7 er
91%[b], 84:16 er

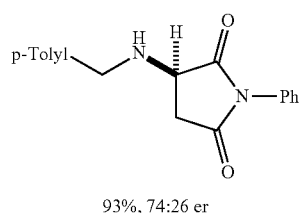

93%, 74:26 er

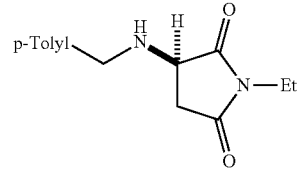

91%, 80:20 er

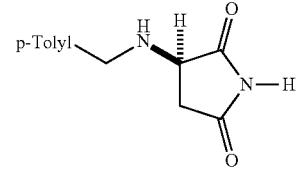

no reaction

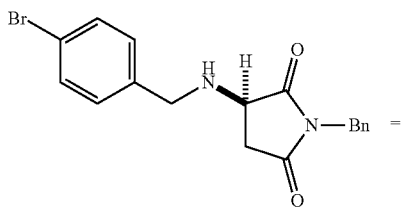

TABLE 2-continued

28

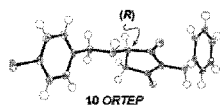

[a]Isolated yields on 0.2 mmol scale.
[b]Reaction run at −40° C. for 24 h. C

29

22

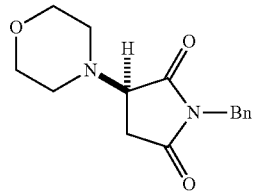

93%, 97:3 er

Acyclic secondary amines showed the lowest selectivity among the nucleophiles (25). Substitutions on the benzyl maleimide were tolerated (26-28). The cross-reaction between piperidine and a substituted benzyl maleimide generated product 29 in good yield and selectivity. N-phenyl maleimide was a poor substrate with regard to selectivity (74:26 e.r.), however the desired 1,4-addition product 30 was synthesized in 93% yield with no observed 1,2-addition product (a common side-reaction with N-aryl maleimides).[22] Maleimide substrates with smaller appendages were observed to react with lower selectivities (31). The unsubstituted maleimide product 32 was not observed, presumably due to a lack of solubility.

The title reaction was successfully scaled up by 1000-fold from the initial screening conditions (Scheme 1). Taking into account the observed dependence of enantioselectivity on concentration, the amine nucleophile was added slowly to the rest of reaction components via cannula. These conditions afforded 7.15 g of the product (93% yield) in 94:6 e.r. The product was successfully recrystallized to >99:1 e.r. Additionally, >95% of the catalyst Ca[B]$_2$ was recovered via column purification. The recovered Ca[B]$_2$ was subsequently able to reproduce the title reaction without loss of yield or selectivity. Our ability to directly recover and reuse Ca[B]$_2$ from each reaction at >95% efficiency lends this methodology more utility, especially given the high molecular weight of the catalyst.

30

31

32

Scheme 1. Reaction scale-up.[a]

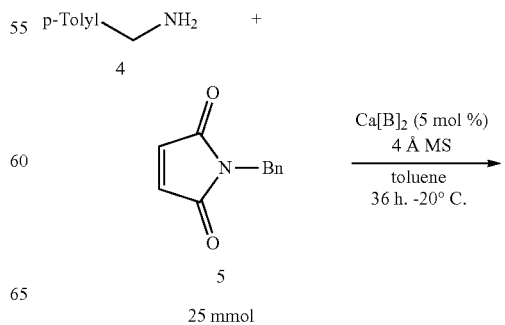

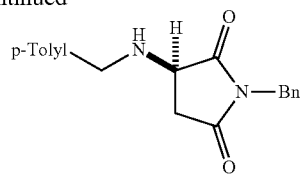

6
93%, 94:6 e.r.
7.15 g
recrystallized: >99:1 e.r.

[a]Isolated yield on 25 mmol scale using 1.1 equivalents of 4. Active catalyst was recovered after chromatography (96%, 1.6 g).

Figure 2:
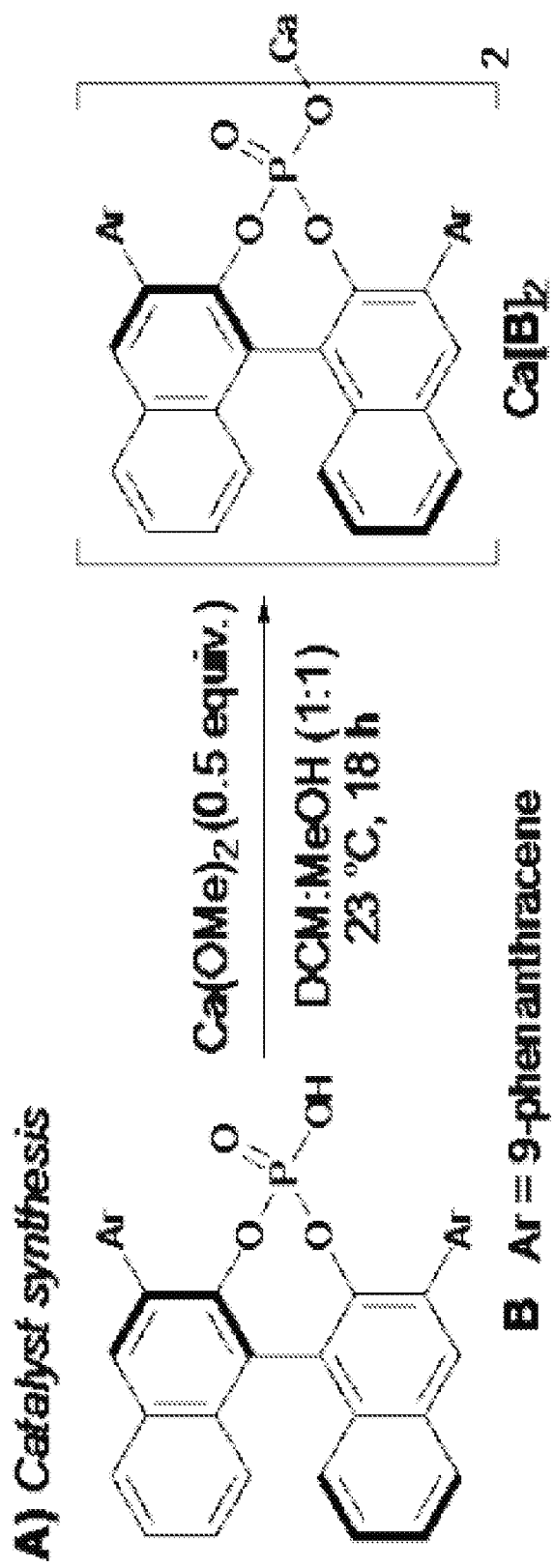
FIG. 2. Synthesis and characterization of Ca[B]$_2$. A) Catalyst synthesis. B) $^{31}$P NMR spectra and ORTEP. C) Enantioselective model.
Figure 2:
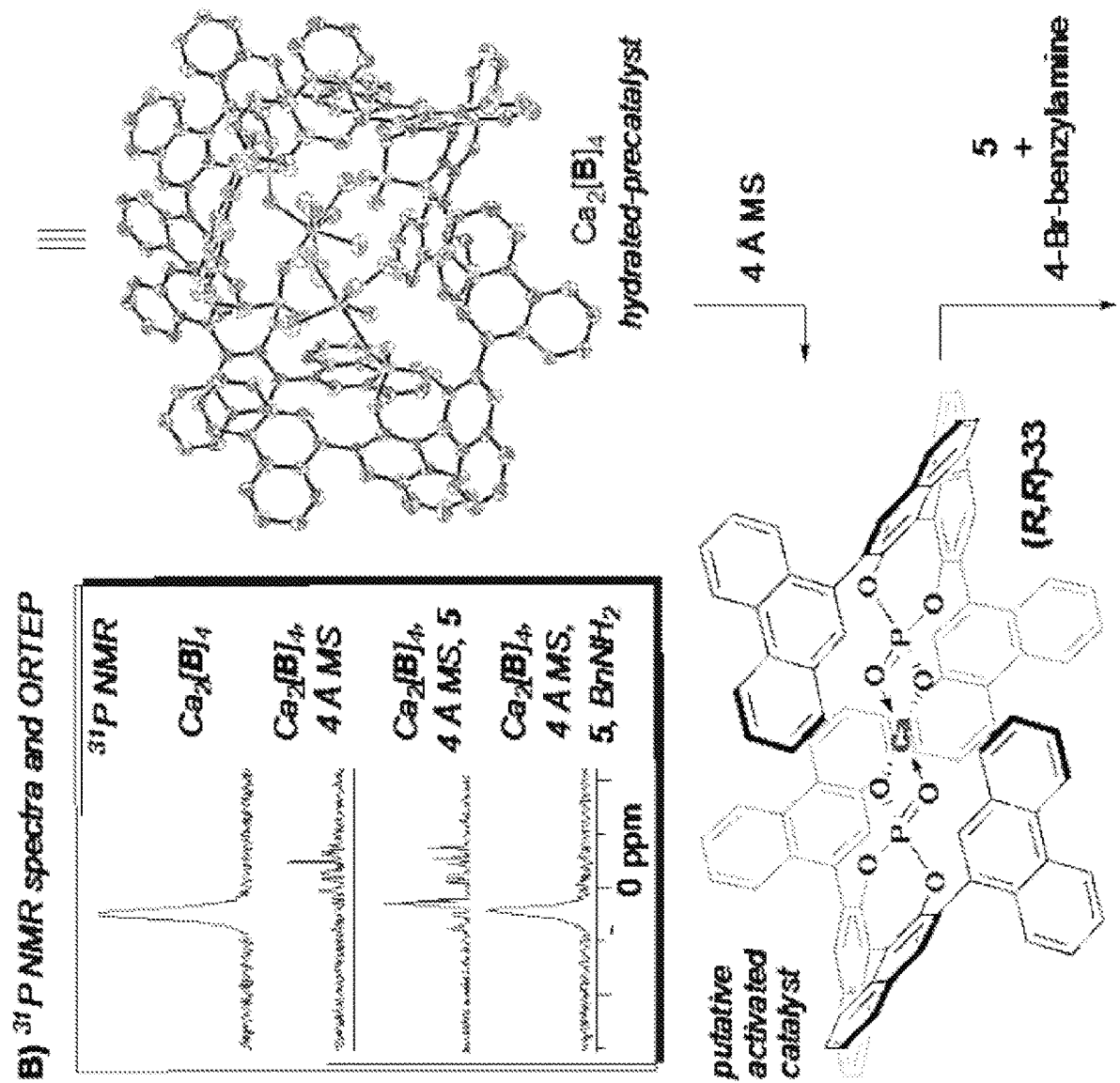
Figure 2:
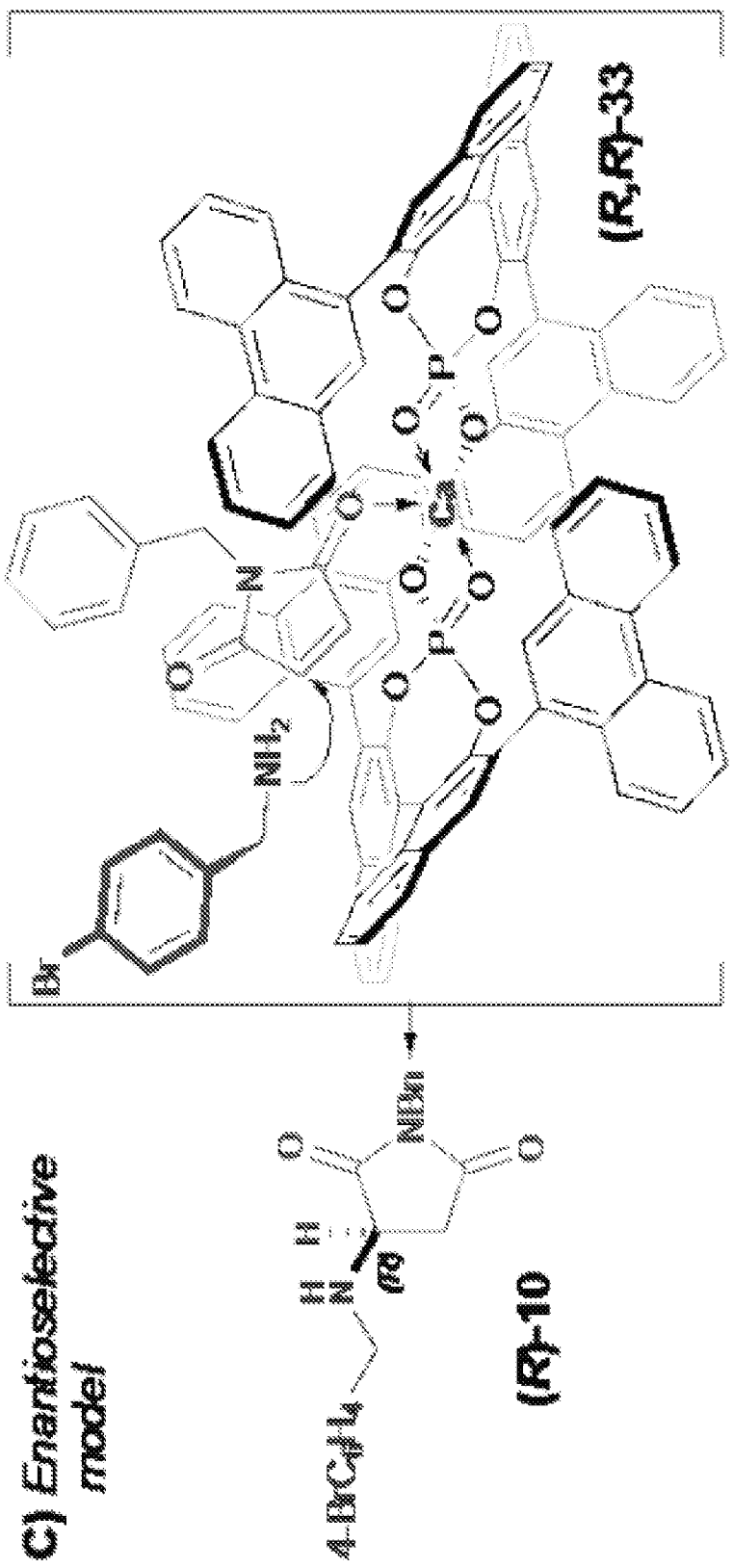

In an effort to rationalize the observed enantioselectivity, we obtained an X-ray crystal structure and $^{31}$P NMR spectroscopy data of the pre-formed calcium phosphate complex used in our optimization and scope studies (FIG. 2B).[23] Surprisingly, the observed structure shows a 4:2 ratio of B to $Ca^{2+}$, not a $Ca[B]_2$ complex. Additionally, both calcium atoms are coordinatively saturated, with each cation bound to five molecules of water, which creates a hydrogen-bonding network. Although it is possible that the observed ORTEP structure is the actual catalytic species, we hypothesize it to be a precatalyst that is activated in the presence of molecular sieves. This observation is supported by a significant change in the $^{31}$P NMR spectrum in the presence of 4 Å MS (FIG. 2B). The yield and selectivity of the reaction also diminished in the absence of 4 Å MS (Table 1, entry 7), supporting that dehydration of the $Ca_2[B]_4 \cdot (H_2O)_{10}$ complex is necessary. Interestingly, when all reaction components are present, the $^{31}$P NMR data is reminiscent of the precatalyst (FIG. 2B). This data could indicate that the presence of the amine re-establishes the hydrogen-bonding network that is lost upon dehydration of the $Ca_2[B]_4 \cdot (H_2O)_{10}$ complex. Understanding how this Lewis base/Lewis acid interaction between active catalyst and a coordinated maleimide substrate will require further investigation.

Based on the obtained spectroscopic data, we hypothesize that the $Ca_2[B]_4 \cdot (H_2O)_{10}$ complex is activated via dehydration in the presence of 4 Å MS, inducing it to reorganize to form $Ca[B]_2$ complex 33 (observed by HRMS, see SI). The extent of dehydration of $Ca_2[B]_4 \cdot (H_2O)_{10}$ required to form the active catalyst cannot be quantified by these experiments, however it is reasonable to postulate that the loss of some coordinating water ligands from the $Ca_2[B]_4 \cdot (H_2O)_{10}$ complex should open up Lewis acidic sites on the calcium atom, which are then able to coordinate the amine nucleophile. Based on structure 33, we propose a model for enantioselectivity where the si-face of maleimide 5 is blocked, allowing for re-face attack of the amine nucleophile (FIG. 2C).

After exploring the scope of our conjugate addition with a variety of amines and maleimides, we also applied our methodology to the synthesis of 35, a potent novel 5-$HT_{2A}$ agonist developed by Acadia pharmaceuticals (Scheme 2).[18c] Since the binding affinity of 35 was measured as a racemic mixture, we envisioned that our methodology could readily determine the more active enantiomer. Starting from recrystallized 6, lithium aluminium hydride reduction cleanly produced 34 in 95% yield and >99:1 e.r. (Scheme 2). Selective acylation of 34 with 4-methoxyphenylacetic acid produced 35 in 43% yield and >99:1 e.r. To further demonstrate the utility of this methodology, we were able to selectively remove the benzylic group on the amine (36) as well as selectively deoxygenate adjacent to the amine (37).

Scheme 2. Substrate diversification and target synthesis.

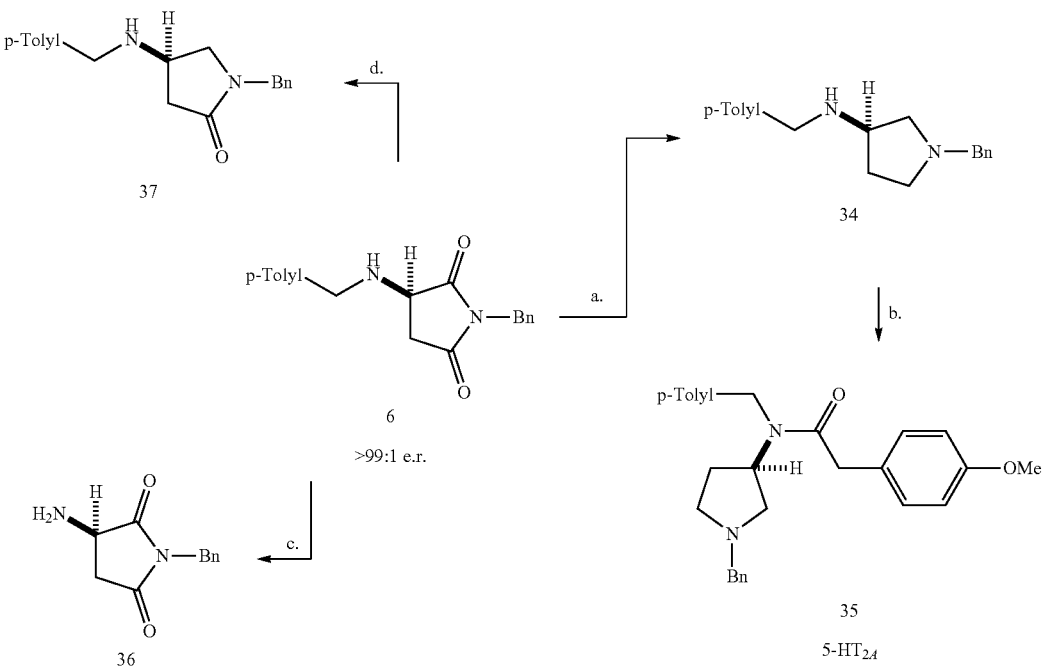

Reagents and conditions: a) LiAlH$_4$, THF, reflux, 95%, >99:1 e.r. b) (4-methoxy)phenylacetyl chloride, DIPEA, 43%, >99:1 e.r. c) Pd/C, H$_2$ (1 atm), MeOH, 96%, >99:1 e.r. d) i. NaBH$_4$, DCM:MeOH, 4° C., 42%; ii. Et$_3$SiH, TFA, DCM, 0° C., 84%, 97:3 e.r.

Conclusions

In summary, we have discovered an efficient and scalable catalytic asymmetric conjugate addition of unmasked and unfunctionalized amines to maleimides. The process accommodates both primary and secondary amines underscoring the unusual compatibility of these Lewis basic nucleophiles with the Lewis acidic $Ca^{2+}$ complex. Crystallographic studies indicate an initial $Ca_2[B]_4$ species is formed through the reaction of a chiral phosphoric acid and calcium(II) methoxide. Further spectroscopic studies indicate that a dynamic process is involved where molecular sieves are required for the observed reactivity and selectivity and are thought to play a role in the activation of the catalyst. The addition of amine nucleophiles can re-establish a hydrogen-bonding network similar to that found in the hydrated $Ca_2[B]_4 \cdot (H_2O)_{10}$ complex. While the calcium phosphate catalyst $Ca[B]_2$ has a relatively high molecular weight, it can be effectively recovered in >95% yield. Future investigations involve continued analysis of calcium-phosphate dynamics and applications of this reaction in synthesis of bioactive compounds.

REFERENCES

1. Chiral Amine Synthesis; Nugent, T. C., Ed.; Wiley-VCH: Weinheim, Germany, 2010.
2. (a) C. C. Price and R. M. Roberts, Journal of the American Chemical Society, 1946, 68, 1204-1208; (b) W. S. Johnson, E. L. Woroch and B. G. Buell, Journal of the American Chemical Society, 1949, 71, 1901-1905; (c) H. B. MacPhillamy, R. L. Dziemian, R. A. Lucas and M. E. Kuehne, Journal of the American Chemical Society, 1958, 80, 2172-2178; (d) S. Kano, T. Ebata and S. Shibuya, Journal of the Chemical Society, Perkin Transactions 1, 1980, 2105-2111.
3. (a) R. Kinas, K. Pankiewicz, W. J. Stec, P. B. Farmer, A. B. Foster and M. Jarman, The Journal of Organic Chemistry, 1977, 42, 1650-1652; (b) J. D'Angelo and J. Maddaluno, Journal of the American Chemical Society, 1986, 108, 8112-8114; (c) G. Jenner, Tetrahedron Letters, 1995, 36, 233-236.
4. (a) M. Furukawa, T. Okawara and Y. Terawaki, CHEMICAL & PHARMACEUTICAL BULLETIN, 1977, 25, 1319-1325; (b) J. M. Hawkins and G. C. Fu, The Journal of Organic Chemistry, 1986, 51, 2820-2822; (c) H. Estermann and D. Seebach, Helvetica Chimica Acta, 1988, 71, 1824-1839; (d) E. Juaristi, J. Escalante, B. Lamatsch and D. Seebach, The Journal of Organic Chemistry, 1992, 57, 2396-2398.
5. (a) S. G. Davies, A. D. Smith and P. D. Price, Tetrahedron: Asymmetry, 2005, 16, 2833-2891; (b) S. G. Davies, A. M. Fletcher, P. M. Roberts and J. E. Thomson, Tetrahedron: Asymmetry, 2012, 23, 1111-1153.
6. (a) M. Liu and M. P. Sibi, Tetrahedron, 2002, 58, 7991-8035; (b) L.-W. Xu and C.-G. Xia, European Journal of Organic Chemistry, 2005, 2005, 633-639; (c) D. Enders, C. Wang and J. X. Liebich, Chemistry—A European Journal, 2009, 15, 11058-11076.
7. (a) M. Kawatsura and J. F. Hartwig, Organometallics, 2001, 20, 1960-1964; (b) J. Liu, H. Li, A. Spannenberg, R. Franke, R. Jackstell and M. Beller, Angewandte Chemie International Edition, 2016, 55, 13544-13548.
8. (a) J. K. Myers and E. N. Jacobsen, Journal of the American Chemical Society, 1999, 121, 8959-8960; (b) D. J. Guerin, T. E. Horstmann and S. J. Miller, Organic Letters, 1999, 1, 1107-1109; (c) T. E. Horstmann, D. J. Guerin and S. J. Miller, Angewandte Chemie International Edition, 2000, 39, 3635-3638; (d) D. J. Guerin and S. J. Miller, Journal of the American Chemical Society, 2002, 124, 2134-2136; (e) M. S. Taylor, D. N. Zalatan, A. M. Lerchner and E. N. Jacobsen, Journal of the American Chemical Society, 2005, 127, 1313-1317; (f) T. Bellavista, S. Meninno, A. Lattanzi and G. Della Sala, Advanced Synthesis & Catalysis, 2015, 357, 3365-3373.
9. (a) M. P. Sibi, J. J. Shay, M. Liu and C. P. Jasperse, Journal of the American Chemical Society, 1998, 120, 6615-6616; (b) N. Yamagiwa, S. Matsunaga and M. Shibasaki, Journal of the American Chemical Society, 2003, 125, 16178-16179; (c) D. Didier, A. Meddour, S. Bezzenine-Lafollée and J. Collin, European Journal of Organic Chemistry, 2011, 2011, 2678-2684; (d) W. Li, X. Yu, Z. Yue and J. Zhang, Organic Letters, 2016, 18, 3972-3975.
10. (a) Y. K. Chen, M. Yoshida and D. W. C. MacMillan, Journal of the American Chemical Society, 2006, 128, 9328-9329; (b) L. Wang, S. Shirakawa and K. Maruoka, Angewandte Chemie International Edition, 2011, 50, 5327-5330; (c) M. Weiβ, S. Borchert, E. Rëmond, S. Jugë and H. Gröger, Heteroatom Chemistry, 2012, 23, 202-209.
11. (a) J. Wang, H. Li, L. Zu and W. Wang, Organic Letters, 2006, 8, 1391-1394; (b) P. Diner, M. Nielsen, M. Mango and K. A. Jorgensen, Angewandte Chemie, 2007, 119, 2029-2033; (c) J. Lv, H. Wu and Y. Wang, European Journal of Organic Chemistry, 2010, 2010, 2073-2083.
12. D. Enders, C. Wang and G. Raabe, Synthesis, 2009, 2009, 4119-4124.
13. (a) D. Uraguchi, D. Nakashima and T. Ooi, Journal of the American Chemical Society, 2009, 131, 7242-7243; (b) H.-M. Yang, L. Li, F. Li, K.-Z. Jiang, J.-Y. Shang, G.-Q. Lai and L.-W. Xu, Organic Letters, 2011, 13, 6508-6511.
14. (a) Y. Hamashima, H. Somei, Y. Shimura, T. Tamura and M. Sodeoka, Organic Letters, 2004, 6, 1861-1864; (b) P. H. Phua, A. J. P. White, J. G. de Vries and K. K. Hii, Advanced Synthesis & Catalysis, 2006, 348, 587-592.
15. (a) G. Sundararajan and N. Prabagaran, Organic Letters, 2001, 3, 389-392; (b) L. Fadini and A. Togni, Chemical Communications, 2003, 30-31; (c) L. Wang, J. Chen and Y. Huang, Angewandte Chemie International Edition, 2015, 54, 15414-15418.
16. E. M. Phillips, M. Riedrich and K. A. Scheidt, Journal of the American Chemical Society, 2010, 132, 13179-13181.
17. (a) D. Bouzard, P. Di Cesare, M. Essiz, J. P. Jacquet, B. Ledoussal, P. Remuzon, R. E. Kessler and J. Fung-Tomc, Journal of Medicinal Chemistry, 1992, 35, 518-525; (b) C. T. Hoang, V. H. Nguyen, V. Alezra and C. Kouklovsky, The Journal of Organic Chemistry, 2008, 73, 1162-1164; (c) D. G. Washburn, T. H. Hoang, J. S. Frazee, L. Johnson, M. Hammond, S. Manns, K. P. Madauss, S. P. Williams, C. Duraiswami, T. B. Tran, E. L. Stewart, E. T. Grygielko, L. E. Glace, W. Trizna, R. Nagilla, J. D. Bray and S. K. Thompson, Bioorganic & Medicinal Chemistry Letters, 2009, 19, 4664-4668; (d) S. K. Thompson, D. G. Washburn, J. S. Frazee, K. P. Madauss, T. H. Hoang, L. Lapinski, E. T. Grygielko, L. E. Glace, W. Trizna, S. P. Williams, C. Duraiswami, J. D. Bray and N. J. Laping, Bioorganic & Medicinal Chemistry Letters, 2009, 19, 4777-4780.
18. For select examples of bioactive aminosuccinimides and aminosuccinimide derivatives, see: a) Y. J. Zhang, Z. Wang, D. Sprous, R. Nabioullin, Bioorg. Med. Chem. Lett. 2006, 16, 525-528; b) K. Chiyoda, J. Shimokawa, T. Fukuyama, Angew. Chem. Int. Ed. 2012, 51, 2505-2508. (c) C. M. A Andersson, G. Croston, E. L. Hansen, A. K. Uldam, US 2002/0004513 A1. (d) T. Abraham, B. P. Kashinath, L. V. S. P. Rao, WO 2004/022536 A1. (e) T. T. Wagner, H. R. Howard, US 2006/0019998 A1. (f) D. King, L. A. Thompson, J. Shi, S. Thangathirupathy, J. S. Warner, I. Islam, J. E. Macor, US 2015/0191452 A1.
19. (a) S. Harder, Chemical Reviews, 2010, 110, 3852-3876; (b) S. Kobayashi and Y. Yamashita, Accounts of Chemical Research, 2011, 44, 58-71; (c) J. M. Begouin and M. Niggemann, Chemistry—A European Journal, 2013, 19, 8030-8041; (d) V. J. Meyer, L. Fu, F. Marquardt and M.

Niggemann, Advanced Synthesis & Catalysis, 2013, 355, 1943-1947; (e) C. C. Dulin, K. L. Murphy and K. A. Nolin, Tetrahedron Letters, 2014, 55, 5280-5282; (f) J. Davies and D. Leonori, Chemical Communications, 2014, 50, 15171-15174; (g) D. Lebœuf, E. Schulz and V. Gandon, Organic Letters, 2014, 16, 6464-6467; (h) S. Shimizu, T. Tsubogo, P. Xu and S. Kobayashi, Organic Letters, 2015, 17, 2006-2009; (i) L. C. Wilkins and R. L. Melen, Coordination Chemistry Reviews, 2016, 324, 123-139; (j) A. Domźalska, A. Ulikowski and B. Furman, in Chiral Lewis Acids in Organic Synthesis, Wiley-VCH Verlag GmbH & Co. KGaA, 2017, pp. 1-25.
20. (a) M. Hatano, T. Ikeno, T. Matsumura, S. Torii and K. Ishihara, Advanced Synthesis & Catalysis, 2008, 350, 1776-1780; (b) M. Hatano, K. Moriyama, T. Maki and K. Ishihara, Angewandte Chemie International Edition, 2010, 49, 3823-3826; (c) M. Rueping, B. J. Nachtsheim, R. M. Koenigs and W. Ieawsuwan, Chemistry—A European Journal, 2010, 16, 13116-13126; (d) G. K. Ingle, Y. Liang, M. G. Mormino, G. Li, F. R. Fronczek and J. C. Antilla, Organic Letters, 2011, 13, 2054-2057; (e) M. Rueping, T. Bootwicha and E. Sugiono, Synlett, 2011, 2011, 323-326; (f) Z. Zhang, W. Zheng and J. C. Antilla, Angewandte Chemie International Edition, 2011, 50, 1135-1138; (g) W. Zheng, Z. Zhang, M. J. Kaplan and J. C. Antilla, Journal of the American Chemical Society, 2011, 133, 3339-3341; (h) M. Rueping, T. Bootwicha, S. Kambutong and E. Sugiono, Chemistry—An Asian Journal, 2012, 7, 1195-1198; (i) G. Li, T. Liang, L. Wojtas and J. C. Antilla, Angewandte Chemie International Edition, 2013, 52, 4628-4632;
(j) T. Liang, G. Li, L. Wojtas and J. C. Antilla, Chemical Communications, 2014, 50, 14187-14190; (k) A. Lee and K. A. Scheidt, Angewandte Chemie International Edition, 2014, 53, 7594-7598; (l) D. Parmar, E. Sugiono, S. Raja and M. Rueping, Chemical Reviews, 2014, 114, 9047-9153; (m) C. Lalli, A. Dumoulin, C. Lebée, F. Drouet, V. Guérineau, D. Touboul, V. Gandon, J. Zhu and G. Masson, Chemistry—A European Journal, 2015, 21, 1704-1712.
21. J. Maddaluno, A. Corruble, V. Leroux, G. Plé and P. Duhamel, Tetrahedron: Asymmetry, 1992, 3, 1239-1242.
22. (a) P. R. Ashton, P. Calcagno, N. Spencer, K. D. M. Harris and D. Philp, Organic Letters, 2000, 2, 1365-1368; (b) Y. Bi, L. Bailly, F. Marsais, V. Levacher, C. Papamicaël and G. Dupas, Tetrahedron: Asymmetry, 2004, 15, 3703-3706.
23. CCDC 1531265 contains the supplementary crystallographic data for Ca[B]$_2$. CCDC 1548340 contains the supplementary crystallographic data for compound 10. These data can be obtained free of charge from The Cambridge Crystallographic Data Centre via www.ccdc.cam.ac.uk/data_request/cif.

Example 2—Supporting Information for Example 1

General Information

All reactions were carried out under an ambient atmosphere in non-oven-dried glassware with magnetic stirring. THF, toluene, and DMF were purified by passage through a bed of activated alumina.[1] Reagents were purified prior to use unless otherwise stated following the guidelines of Perrin and Armarego.[2] N-tolylamine was distilled from CaH$_2$. Purification of reaction products was carried out by flash chromatography using EM Reagent silica gel 60 (230-400 mesh). Analytical thin layer chromatography was performed on EM Reagent 0.25 mm silica gel 60-F plates. Visualization was accomplished with UV light and ceric ammonium nitrate stain or potassium permanganate stain followed by heating. Infrared spectra were recorded on a Bruker Tensor 37 FT-IR spectrometer. $^1$H NMR spectra were recorded on AVANCE III 500 MHz w/direct cryoprobe (500 MHz) spectrometer and are reported in ppm using solvent as an internal standard (CDCl$_3$ at 7.26 ppm). Data are reported as (ap=apparent, s=singlet, d=doublet, t=apparent triplet, q=quartet, m=multiplet, b=broad; coupling constant(s) in Hz; integration.) Proton-decoupled $^{13}$C NMR spectra were recorded on an AVANCE III 500 MHz w/direct cryoprobe (125 MHz) spectrometer and are reported in ppm using solvent as an internal standard (CDCl$_3$ at 77.00 ppm). $^{31}$P NMR spectra were acquired at 26° C. on a 400 MHz Agilent 400MR-DD2 spectrometer equipped with a OneNMR probe and a 7600AS autosampler; this system was funded by NSF CRIF grant CHE-104873. Mass spectra were obtained on a WATERS Acquity-H UPLC-MS with a single quad detector (ESI) or on a Varian 1200 Quadrupole Mass Spectrometer and Micromass Quadro II Spectrometer (ESI).

Synthesis and Characterization of Ca[B]$_2$

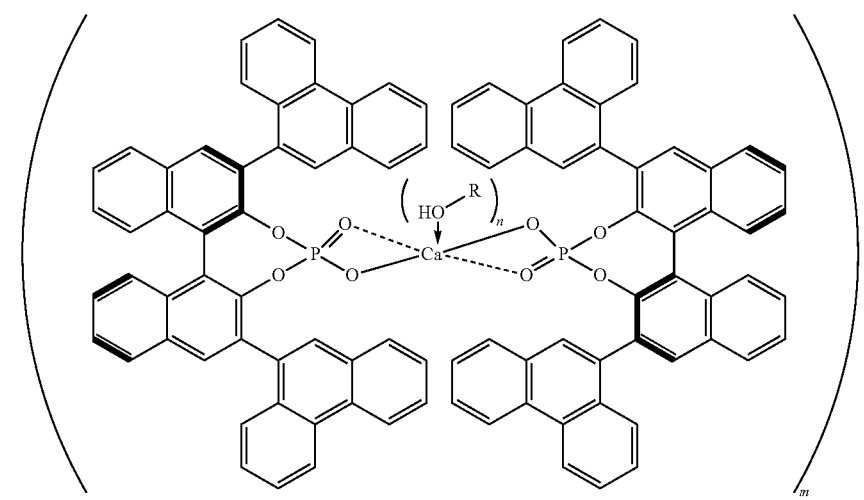

calcium 2,6-dhphenanthren-9-yl)dinaphtho[2,1-d:1',2'-f][1,3,2]dioxaphosphepin-4-olate 4-oxide (Ca[B]$_2$): To a flame-dried flask at 23° C., charged with dichloromethane:MeOH (1:1, 12 mL), was added B [(R) 9,9'-bisphenanthryl-BINOL phosphoric acid (2.57 mmol, 1.80 g, 2.0 equiv)] and freshly powdered calcium methoxide (1.28 mmol, 0.131 g, 1.0 equiv). The reaction was stirred for 24 h at 23° C. at which point the slightly turbid solution was concentrated to dryness, azeotroped with toluene (3×15 mL), and placed under high vacuum (~0.1 Torr) to yield Ca[B]$_2$ as an off white powder (1.28 mmol, 1.84 g, quantitative).

Analytical data for Ca[B]$_2$: $^1$H NMR (500 MHz, DMSO-d$_6$) δ 8.90 (dd, J=14.0, 8.2 Hz, 8H), 8.06 (m, 16H), 7.57 (m, 36H), 4.11 (q, J=5.2 Hz, 1H, MeOH), 3.34 (s, 14H, H$_2$O), 3.17 (d, J=5.0 Hz, 3H, MeOH). $^{13}$C NMR (126 MHz, DMSO-d$_6$) δ 148.4, 148.3, 134.3, 133.3, 132.3, 131.4, 131.2, 130.1, 129.6, 129.6, 129.3, 129.0, 128.3, 126.8, 126.5, 126.3, 124.9, 123.0, 122.7, 122.4, 48.6 (MeOH). HRMS (ESI): Mass calculated for C$_{96}$H$_{57}$CaO$_8$P$_2$ [M+H]: 1439.3155; found: 1439.3149.

General Procedure and Characterization Data for the Synthesis of Aminosuccinimides In a nitrogen-filled dry box, a screw-cap reaction tube equipped with a magnetic stirbar was charged with the corresponding maleimide 2 (0.2 mmol, 1.0 equiv), calcium phosphate complex catalyst Ca[B]$_2$ (14.0 mg, 0.01 mmol, 0.05 equiv), and 4 Å MS (100 mg). The tube was capped with a septum cap, removed from the drybox and put under positive N$_2$ pressure. Dry toluene (3.0 mL) was then added and the heterogeneous mixture was cooled to −20° C. A solution of the corresponding amine (0.20 mmol, 1.0 equiv) in toluene (0.9 mL) was added dropwise, and the reaction was stirred for 14 h at spectrum ° C. At this point an additional bolus of amine (0.02 mmol, 0.1 equiv) in toluene (0.1 mL) was added. After 18 h, the entire crude reaction mixture at −20° C. was directly transferred onto a SiO$_2$ column pre-equilibrated with 3:1 Hex:EtOAc. Flash chromatography (gradient 3:1 Hex:EtOAc→1:1 Hex:EtOAc) afforded the aminosuccinimide product, followed by elution with 10:1 EtOAc:MeOH to recover Ca[B]$_2$.

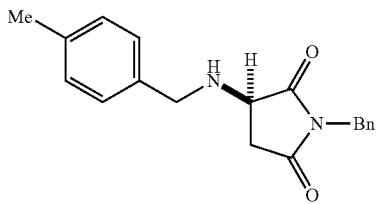 [SMILES: Cc1ccc(CN[C@@H]2CC(=O)N(Cc3ccccc3)C2=O)cc1]

(R)-1-benzyl-3-((4-methylbenzyl)amino)pyrrolidine-2,5-dione (6): Prepared according to the general procedure using p-tolylmethylamine (0.027 g, 0.22 mmol, 1.1 equiv) to afford 0.062 g (87% yield) of product as a clear crystalline solid.

Analytical data for 6: $^1$H NMR (500 MHz, Chloroform-d) δ 7.24 (m, 10H), 4.65 (s, 2H), 3.79 (m, 3H), 2.85 (dd, J=18.0, 8.3 Hz, 1H), 2.51 (dd, J=18.1, 4.8 Hz, 1H), 2.33 (s, 3H), 2.16 (s, 1H). $^{13}$C NMR (126 MHz, Chloroform-d) δ 177.6, 174.9, 137.2, 135.5, 135.5, 129.3, 128.8, 128.7, 128.2, 128.0, 55.4, 51.6, 42.4, 36.4, 21.1. HRMS (ESI): Mass calculated for C$_{19}$H$_{21}$N$_2$O$_2$ [M+H]: 309.1603; found: 309.1603; IR (thin film) 3302, 3291, 2913, 2846, 1763, 1690, 1514, 1495, 1453; Enantiomeric ratio was measured by chiral phase HPLC (AD-H, 10% i-PrOH/Hexanes, 1.0 mL/min, 210 nm), Rt (major)=18.07 Min, Rt (minor)=15.16 Min; e.r.=94:6.

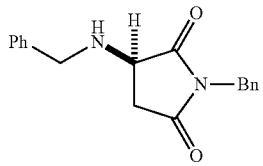 [SMILES: O=C1C[C@@H](NCc2ccccc2)C(=O)N1Cc1ccccc1]

(R)-1-benzyl-3-(benzylamino)pyrrolidine-2,5-dione (7): Prepared according to the general procedure using benzylamine (0.024 g, 0.22 mmol, 1.1 equiv) to afford 0.049 g (84% yield) of product as a clear crystalline solid.

Analytical data for 7: $^1$H NMR (500 MHz, Chloroform-d) δ 7.32 (m, 10H), 4.65 (d, J=2.4 Hz, 2H), 3.86 (q, J=13.1 Hz, 2H), 3.75 (dd, J=8.2, 5.0 Hz, 1H), 2.87 (dd, J=17.9, 8.3 Hz, 1H), 2.52 (dd, J=17.9, 5.0 Hz, 1H), 2.21 (s, 1H).$^{13}$C NMR (126 MHz, Chloroform-d) δ 177.6, 174.8, 138.6, 135.5, 128.8, 128.7 (×2), 128.3, 128.0, 127.6, 55.5, 51.8, 42.4, 36.4. HRMS (ESI): Mass calculated for C$_{18}$H$_{19}$N$_2$O$_2$ [M+H]: 295.1447; found: 295.1445; IR (thin film) 3330, 3028, 2926, 2848, 1694, 1605, 1401, 1426, 1458, 1495, Enantiomeric ratio was measured by chiral phase HPLC (AD-H, 10% i-PrOH/Hexanes, 1.0 mL/min, 210 nm), Rt (major)=18.14 Min, Rt (minor)=14.78 Min; e.r.=94:6.

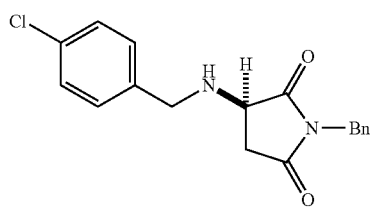

(R)-1-benzyl-3-((4-fluorobenzyl)amino)pyrrolidine-2,5-dione (8): Prepared according to the general procedure using (4-fluorophenyl)methanamine (0.028 g, 0.22 mmol, 1.1 equiv) to afford 0.048 g (77% yield) of product as a clear crystalline solid.

Analytical data for 8: $^1$H NMR (500 MHz, Chloroform-d) δ 7.32 (m, 7H), 7.01 (m, 2H), 4.65 (d, J=2.0 Hz, 2H), 3.83 (s, 2H), 3.75 (dd, J=8.3, 5.0 Hz, 1H), 2.88 (dd, J=17.9, 8.3 Hz, 1H), 2.50 (dd, J=17.9, 5.0 Hz, 1H), 2.14 (s, 1H). $^{13}$C NMR (126 MHz, Chloroform-d) δ 177.5, 174.7, 162.2 (d, J($^{13}$C-$^{19}$F)=245.7 Hz), 135.5, 134.5 (d, J($^{13}$C-$^{19}$F)=3.2 Hz), 129.9 (d, J($^{13}$C-$^{19}$F)=8.1 Hz), 128.8, 128.7, 128.1, 115.5 (d, J($^{13}$C-$^{19}$F)=21.4 Hz), 55.6, 51.1, 42.5, 36.4; HRMS (ESI): Mass calculated for C$_{18}$H$_{18}$FN$_2$O$_2$ [M+H]: 313.1352; found: 313.1347; IR (thin film) 3300, 3035, 2845, 2912, 1598, 1507, 1482, 1446, 1429, 1401, 1357. Enantiomeric ratio was measured by chiral phase HPLC (AD-H, 10% i-PrOH/Hexanes, 1.0 mL/min, 210 nm), Rt (major)=20.17 Min, Rt (minor)=15.66 Min; e.r.=93:7.

(R)-1-benzyl-3-((4-fluorobenzyl)amino)pyrrolidine-2,5-dione (9): Prepared according to the general procedure using (4-chlorophenyl)methanamine (0.031 g, 0.22 mmol, 1.1 equiv) to afford 0.060 g (91% yield) of product as a clear crystalline solid.

Analytical data for 9: $^1$H NMR (500 MHz, Chloroform-d) δ 7.28 (m, 9H), 4.62 (d, J=1.9 Hz, 2H), 3.80 (s, 2H), 3.71 (dd, J=8.3, 5.0 Hz, 1H), 2.84 (dd, J=17.9, 8.3 Hz, 1H), 2.46 (dd, J=17.9, 5.0 Hz, 1H), 2.11 (s, 1H). $^{13}$C NMR (126 MHz, Chloroform-d) δ 177.5, 174.7, 137.2, 135.4, 133.3, 129.6, 128.8, 128.8, 128.7, 128.1, 55.5, 51.1, 42.5, 36.4 HRMS (ESI): Mass calculated for $C_{18}H_{18}ClN_2O_2$ [M+H]: 329.1057; found: 329.1051; IR (thin film): 3302, 3036, 2911, 2833, 1690, 1445, 1429, 1400, 1335. Enantiomeric ratio was measured by chiral phase HPLC (AD-H, 10% i-PrOH/Hexanes, 1.0 mL/min, 210 nm), Rt (major)=22.05 Min, Rt (minor)=18.0 Min; e.r.=93:7.

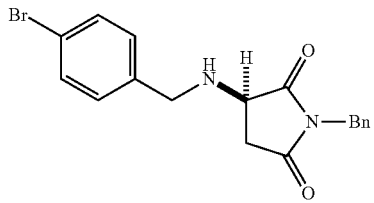 [SMILES: O=C1C[C@@H](NCc2ccc(Cl)cc2)C(=O)N1Cc1ccccc1]

(R)-1-benzyl-3-((4-bromobenzyl)amino)pyrrolidine-2,5-dione (10): Prepared according to the general procedure using (4-bromophenyl)methanamine (0.041 g, 0.22 mmol, 1.1 equiv) to afford 0.067 g (90% yield) of product as a clear crystalline solid.

Analytical data for 10: $^1$H NMR (500 MHz, Chloroform-d) δ 7.45 (m, 2H), 7.37 (dd, J=7.9, 1.7 Hz, 2H), 7.30 (m, 3H), 7.18 (d, J=8.1 Hz, 2H), 4.65 (d, J=2.1 Hz, 2H), 3.82 (s, 2H), 3.74 (dd, J=8.3, 5.0 Hz, 1H), 2.87 (dd, J=18.0, 8.3 Hz, 1H), 2.49 (dd, J=18.0, 5.0 Hz, 1H), 2.13 (s, 1H).$^{13}$C NMR (126 MHz, Chloroform-d) δ 177.5, 174.6, 137.7, 135.4, 131.7, 129.9, 128.8, 128.7, 128.1, 121.4, 55.5, 51.2, 42.5, 36.4. HRMS (ESI): Mass calculated for $C_{18}H_{18}BrN_2O_2$ [M+H]: 373.0552; found: 373.0546; IR (thin film) 3300, 3010, 2833, 1690, 1487, 1466, 1454, 14229, 1402, 1361. Enantiomeric ratio was measured by chiral phase HPLC (AD-H, 10% i-PrOH/Hexanes, 1.0 mL/min, 210 nm), Rt (major)=22.34 Min, Rt (minor)=18.30 Min; e.r.=93:7.

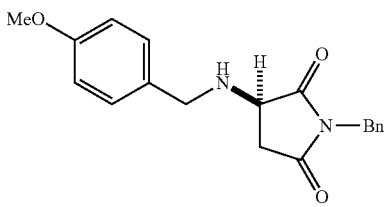 [SMILES: COc1ccc(CN[C@@H]2CC(=O)N(Cc3ccccc3)C2=O)cc1]

(R)-1-benzyl-3-((4-methoxybenzyl)amino)pyrrolidine-2,5-dione (11): Prepared according to the general procedure using (4-methoxyphenyl)methanamine (0.030 g, 0.22 mmol, 1.1 equiv) to afford 0.058 g (90% yield) of product as a clear crystalline solid.

Analytical data for 11: $^1$H NMR (500 MHz, Chloroform-d) δ 7.36 (m, 2H), 7.30 (m, 4H), 7.21 (d, J=8.5 Hz, 2H), 6.86 (d, J=8.6 Hz, 2H), 4.65 (d, J=2.4 Hz, 2H), 3.79 (m, 6H), 2.85 (dd, J=17.9, 8.3 Hz, 1H), 2.50 (dd, J=18.0, 5.0 Hz, 1H); $^{13}$C NMR (126 MHz, Chloroform-d) δ 177.7, 174.9, 159.0, 135.5, 130.7, 129.5, 128.8, 128.7, 128.0, 114.0, 55.4, 55.3, 51.3, 42.4, 36.4; HRMS (ESI): Mass calculated for $C_{19}H_{20}N_2O_3Na$ [M+Na]: 347.1372; found: 347.1366; IR (thin film) 3301, 3050, 2836, 2957, 1689, 1607, 1401, 1428, 1445, 1482, 1513, 1581. Enantiomeric ratio was measured by chiral phase HPLC (AD-H, 10% i-PrOH/Hexanes, 1.0 mL/min, 210 nm), Rt (major)=26.30 Min, Rt (minor)=20.72 Min; e.r.=94:6.

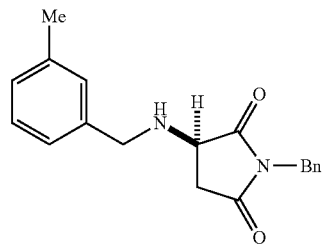 [SMILES: Cc1cccc(CN[C@@H]2CC(=O)N(Cc3ccccc3)C2=O)c1]

(R)-1-benzyl-3-((3-methylbenzyl)amino)pyrrolidine-2,5-dione (12): Prepared according to the general procedure using (3-methylphenyl)methanamine (0.027 g, 0.22 mmol, 1.1 equiv) to afford 0.059 g (96% yield) of product as a clear crystalline solid.

Analytical data for 12: $^1$H NMR (500 MHz, Chloroform-d) δ 7.37 (m, 2H), 7.30 (m, 3H), 7.22 (t, J=7.5 Hz, 1H), 7.09 (m, 3H), 4.65 (d, J=2.4 Hz, 2H), 3.77 (m, 3H), 2.87 (dd, J=18.0, 8.2 Hz, 1H), 2.52 (dd, J=17.9, 5.0 Hz, 1H), 2.34 (s, 3H), 2.21 (s, 1H). $^{13}$C NMR (126 MHz, Chloroform-d) δ 177.6, 174.9, 138.5, 138.4, 135.5, 129.0, 128.8, 128.7, 128.5, 128.3, 128.0, 125.3, 55.5, 51.8, 42.4, 36.4, 21.4. HRMS (ESI): Mass calculated for $C_{19}H_{21}N_2O_2$ [M+H]: 309.1603; found: 309.1598; IR (thin film) 3289, 3009, 2810, 1689, 1607, 1432, 1453, 1496, 1513; Enantiomeric ratio was measured by chiral phase HPLC (AD-H, 10% i-PrOH/Hexanes, 1.0 mL/min, 210 nm), Rt (major)=14.20 Min, Rt (minor)=11.72 Min; e.r.=95:5.

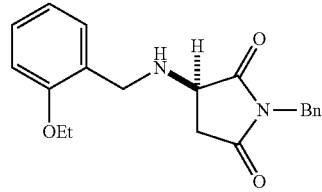 [SMILES: CCOc1ccccc1CN[C@@H]1CC(=O)N(Cc2ccccc2)C1=O]

(R)-1-benzyl-3-((2-ethoxybenzyl)amino)pyrrolidine-2,5-dione (13): Prepared according to the general procedure using (2-ethoxyphenyl)methanamine (0.033 g, 0.22 mmol, 1.1 equiv) to afford 0.062 g (92% yield) of product as a clear crystalline solid.

Analytical data for 13: $^1$H NMR (500 MHz, Chloroform-d) δ 7.35 (m, 2H), 7.26 (m, 4H), 7.17 (dd, J=7.4, 1.7 Hz, 1H), 6.88 (m, 2H), 4.64 (m, 2H), 4.08 (q, J=7.0 Hz, 2H), 3.95 (d, J=13.5 Hz, 1H), 3.73 (d, J=13.5 Hz, 1H), 3.66 (dd, J=8.1, 4.8 Hz, 1H), 2.88 (dd, J=17.8, 8.1 Hz, 1H), 2.58 (m, 2H), 1.45 (t, J=6.9 Hz, 3H).$^{13}$C NMR (126 MHz, Chloroform-d) δ 177.7, 175.2, 157.2, 135.5, 130.2, 128.9, 128.7, 128.6, 127.9, 126.5, 120.4, 111.3, 63.5, 54.8, 47.4, 42.4, 36.3, 14.9. HRMS (ESI): Mass calculated for $C_{20}H_{23}N_2O_3$ [M+H]: 339.1709; found: 339.1906; IR (thin film) 2933, 1699, 1430, 1354, 1476, 1493, 1587, 1599. Enantiomeric ratio was measured by chiral phase HPLC (AD-H, 10% i-PrOH/Hexanes, 0.5 mL/min, 210 nm), Rt (major)=31.75 Min, Rt (minor)=33.25 Min; e. r.=97:3.

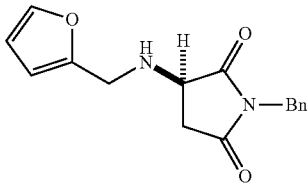 [SMILES: O=C1C[C@@H](NCc2ccco2)C(=O)N1Cc1ccccc1]

(R)-1-benzyl-3-((furan-2-ylmethyl)amino)pyrrolidine-2,5-dione (14): Prepared according to the general procedure using furan-2-ylmethanamine (0.021 g, 0.22 mmol, 1.1 equiv) to afford 0.028 g (49% yield) of product as a clear oil.

Analytical data for 14: $^1$H NMR (500 MHz, Chloroform-d) δ 7.22 (m, 6H), 6.16 (m, 2H), 4.53 (d, J=1.9 Hz, 2H), 3.77 (m, 2H), 3.62 (dd, J=8.2, 5.0 Hz, 1H), 2.76 (dd, J=17.9, 8.2 Hz, 1H), 2.36 (dd, J=18.0, 5.1 Hz, 1H), 2.23 (m, 1H). $^{13}$C NMR (126 MHz, Chloroform-d) δ 177.3, 174.7, 152.1, 142.4, 135.4, 128.8, 128.6, 128.0, 110.3, 108.0, 55.0, 44.1, 42.4, 36.2; HRMS (ESI): Mass calculated for $C_{16}H_{17}N_2O_3$ [M+H]: 285.1239; found: 285.1232; IR (thin film) 3291, 3010, 2982, 2850, 1690, 1604, 1505, 1494, 1456, 1432; Enantiomeric ratio was measured by chiral phase HPLC (AD-H, 10% i-PrOH/Hexanes, 1.0 mL/min, 210 nm), Rt (major)=19.49 Min, Rt (minor)=17.13 Min; e.r.=88:12.

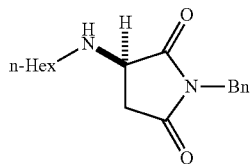

(R)-1-benzyl-3-(hexylamino)pyrrolidine-2,5-dione (15): Prepared according to the general procedure using n-hexylamine (0.022 g, 0.22 mmol, 1.1 equiv) to afford 0.036 g (63% yield) of product as a clear oil.

Analytical data for 15: $^1$H NMR (500 MHz, Chloroform-d) δ 7.32 (m, 5H), 4.65 (s, 2H), 3.75 (dd, J=8.3, 4.9 Hz, 1H), 2.92 (dd, J=18.0, 8.3 Hz, 1H), 2.65 (dt, J=11.1, 7.1 Hz, 1H), 2.54 (m, 2H), 1.83 (s, 1H), 1.47 (q, J=7.3 Hz, 2H), 1.29 (m, 7H), 0.88 (t, J=6.8 Hz, 3H). $^{13}$C NMR (126 MHz, CDCl$_3$) δ=177.7, 175.0, 135.5, 128.8, 128.7, 128.0, 56.4, 47.7, 42.4, 36.3, 31.6, 29.9, 26.8, 22.5, 14.0. HRMS (ESI): Mass calculated for $C_{17}H_{25}N_2O_2$ [M+H]: 289.1916; found: 289.1911; IR (thin film) 3298, 3031, 2952, 2928, 2849, 1694, 1494, 1465, 1455, 1430; Enantiomeric ratio was measured by chiral phase HPLC (AD-H, 10% i-PrOH/Hexanes, 1.0 mL/min, 210 nm), Rt (major)=11.37 Min, Rt (minor)=9.12 Min; e.r.=92:8.

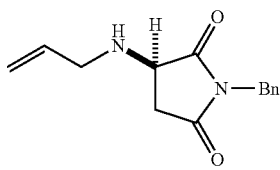 [SMILES: C=CCN[C@@H]1CC(=O)N(Cc2ccccc2)C1=O]

(R)-1-benzyl-3-(propylamino)pyrrolidine-2,5-dione (16): Prepared according to the general procedure using allylamine (0.013 g, 0.22 mmol, 1.1 equiv) to afford 0.048 g (97% yield) of product as a clear solid.

Analytical data for 16: $^1$H NMR (500 MHz, Chloroform-d) δ 7.37 (d, J=6.8 Hz, 2H), 7.30 (m, 3H), 5.85 (ddt, J=16.5, 10.3, 6.1 Hz, 1H), 5.18 (m, 2H), 4.65 (s, 2H), 3.79 (dd, J=8.3, 5.0 Hz, 1H), 3.30 (m, 2H), 2.91 (dd, J=17.9, 8.3 Hz, 1H), 2.53 (dd, J=18.0, 5.0 Hz, 1H), 1.94 (s, 1H). $^{13}$C NMR (126 MHz, Chloroform-d)$^{13}$C NMR, δ 177.6, 174.8, 135.5, 135.4, 128.8, 128.7, 128.0, 117.3, 55.5, 50.3, 42.4, 36.5. HRMS (ESI): Mass calculated for $C_{14}H_{17}N_2O_2$ [M+H]: 245.1290; found: 245.1285; IR (thin film): 3301, 3035, 2928, 2855, 1690, 1497, 1455, 1430, 1397; Enantiomeric ratio was measured by chiral phase HPLC (AD-H, 10% i-PrOH/Hexanes, 1.0 mL/min, 210 nm), Rt (major)=13.87 Min, Rt (minor)=11.63 Min; e.r.=91:9.

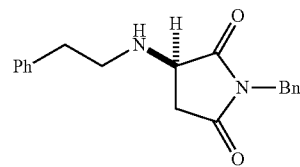 [SMILES: O=C1C[C@@H](NCCc2ccccc2)C(=O)N1Cc1ccccc1]

(R)-1-benzyl-3-(phenethylamino)pyrrolidine-2,5-dione (17): Prepared according to the general procedure using phenethylamine (0.027 g, 0.22 mmol, 1.1 equiv) to afford 0.062 g (81% yield) of product as a clear solid.

Analytical data for 17: $^1$H NMR (500 MHz, Chloroform-d) δ 7.33 (m, 7H), 7.21 (m, 3H), 4.64 (d, J=1.6 Hz, 2H), 3.75 (dd, J=8.3, 4.9 Hz, 1H), 2.88 (m, 5H), 2.50 (dd, J=18.0, 4.9 Hz, 1H), 1.85 (s, 1H). $^{13}$C NMR (126 MHz, Chloroform-d) δ 177.4, 174.8, 139.1, 135.5, 128.8, 128.7, 128.6, 128.6, 128.0, 126.5, 56.3, 48.8, 42.4, 36.2, 36.2; HRMS (ESI): Mass calculated for $C_{19}H_{21}N_2O_2$ [M+H]: 309.1603; found: 309.1598; IR (thin film) 330, 3028, 2918, 2860, 1693, 1604, 1497, 1465, 1453, 1431. Enantiomeric ratio was measured by chiral phase HPLC (AD-H, 10% i-PrOH/Hexanes, 1.0 mL/min, 210 nm), Rt (major)=17.06 Min, Rt (minor)=14.05 Min; e.r.=88:12.

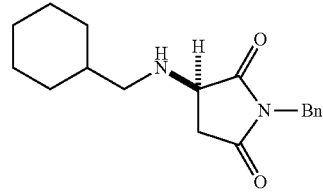 [SMILES: O=C1C[C@@H](NCC2CCCCC2)C(=O)N1Cc1ccccc1]

(R)-1-benzyl-3-((cyclohexylmethyl)amino)pyrrolidine-2,5-dione (18): Prepared according to the general procedure using cyclohexylmethanamine (0.025 g, 0.22 mmol, 1.1 equiv) to afford 0.058 g (97% yield) of product as a clear solid.

Analytical data for 18: $^1$H NMR (500 MHz, Chloroform-d) δ 7.33 (m, 5H), 4.65 (d, J=1.9 Hz, 2H), 3.73 (dd, J=8.3, 4.9 Hz, 1H), 2.91 (dd, J=18.0, 8.3 Hz, 1H), 2.50 (dt, J=17.8, 5.5 Hz, 2H), 2.37 (dd, J=11.3, 6.7 Hz, 1H), 1.83 (s, 1H), 1.71 (m, 5H), 1.41 (m, 1H), 1.20 (m, 3H), 0.90 (m, 2H). $^{13}$C NMR (126 MHz, CDCl$_3$) δ=177.7, 175.0, 135.5, 128.8, 128.6, 128.0, 56.5, 54.2, 42.4, 38.0, 36.3, 31.2, 26.5, 25.9. Mass calculated for $C_{18}H_{25}N_2O_2$ [M+H]: 301.1916; found: 301.1911; IR (thin film) 3303, 2916, 2850, 1694, 1494, 1461, 1431; Enantiomeric ratio was measured by chiral phase HPLC (AD-H, 10% i-PrOH/Hexanes, 1.0 mL/min, 210 nm), Rt (major)=9.75 Min, Rt (minor)=9.18 Min; e. r.=97:3.

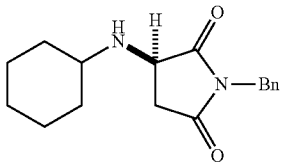 [SMILES: O=C1C[C@@H](NC2CCCCC2)C(=O)N1Cc1ccccc1]

(R)-1-benzyl-3-(cyclohexylamino)pyrrolidine-2,5-dione (19): Prepared according to the general procedure using cyclohexylamine (0.022 g, 0.22 mmol, 1.1 equiv) to afford 0.048 g (84% yield) of product as a clear solid.

Analytical data for 19: $^1$H NMR (500 MHz, Chloroform-d) δ 7.32 (m, 5H), 4.65 (s, 2H), 3.86 (dd, J=8.2, 5.0 Hz, 1H), 2.93 (dd, J=17.9, 8.2 Hz, 1H), 2.54 (m, 2H), 1.86 (m, 2H), 1.60 (m, 3H), 1.18 (m, 5H). $^{13}$C NMR (126 MHz, CDCl$_3$) δ 178.2, 175.0, 135.5, 128.9, 128.7, 128.0, 55.7, 54.2, 42.5, 38.1, 34.1, 33.1, 25.8, 24.9, 24.9. HRMS (ESI): Mass calculated for C$_{17}$H$_{23}$N$_2$O$_2$ [M+H]: 287.1760; found: 287.1754; IR (thin film) 3520, 3248, 3035, 2920, 2849, 1688, 1630, 1520, 1498, 1470, 1455, 1439, 1401; Enantiomeric ratio was measured by chiral phase supercritical fluid HPLC (IA, 2% MeOH/CO$_2$, 1.0 mL/min, 210 nm), Rt (major)=2.16 Min, Rt (minor)=2.38 Min; e.r.=95:5.

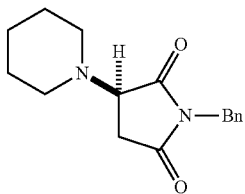 [SMILES: O=C1C[C@@H](N2CCCCC2)C(=O)N1Cc1ccccc1]

(R)-1-benzyl-3-(piperidin-1-yl)pyrrolidine-2,5-dione (20): Prepared according to the general procedure using piperidine (0.019 g, 0.22 mmol, 1.1 equiv) to afford 0.052 g (95% yield) of product as a clear oil.

Analytical data for 20: $^1$H NMR (500 MHz, Chloroform-d) δ 7.32 (m, 5H), 4.64 (m, 2H), 3.77 (dd, J=9.1, 4.7 Hz, 1H), 2.82 (dd, J=18.6, 9.0 Hz, 1H), 2.69 (m, 3H), 2.41 (dt, J=11.0, 5.3 Hz, 2H), 1.59 (m, 4H), 1.43 (p, J=6.0 Hz, 2H). $^{13}$C NMR (126 MHz, CDCl$_3$) δ 176.2, 175.0, 135.8, 128.8, 128.6, 127.9, 63.2, 50.2, 42.1, 31.6, 26.0, 24.0. HRMS (ESI): Mass calculated for C$_{16}$H$_{21}$N$_2$O$_2$ [M+H]: 273.1603; found: 273.1598; IR (thin film) 2934, 2846, 1691, 1499, 1470, 1454, 1441, 1422; Enantiomeric ratio was measured by chiral phase HPLC (AD-H, 10% i-PrOH/Hexanes, 1.0 mL/min, 210 nm), Rt (major)=23.70 Min, Rt (minor)=27.27 Min; e.r.=97:3.

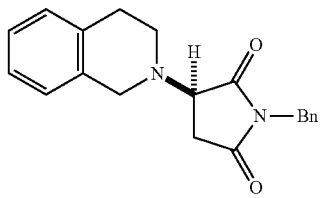 [SMILES: O=C1C[C@@H](N2CCc3ccccc3C2)C(=O)N1Cc1ccccc1]

(R)-1-benzyl-3-(3,4-dihydroisoquinolin-2(1H)-yl)pyrrolidine-2,5-dione (21): Prepared according to the general procedure using 1,2,3,4-tetrahydroisoquinoline (0.029 g, 0.22 mmol, 1.1 equiv) to afford 0.045 g (71% yield) of product as a clear oil.

Analytical data for 21: $^1$H NMR (500 MHz, Chloroform-d) δ 7.40 (m, 2H), 7.31 (m, 3H), 7.11 (m, 3H), 6.95 (m, 1H), 4.69 (m, 2H), 4.05 (d, J=14.3 Hz, 1H), 3.97 (dd, J=9.0, 4.7 Hz, 1H), 3.70 (d, J=14.3 Hz, 1H), 2.87 (m, 6H). $^{13}$C NMR (126 MHz, CDCl$_3$) δ $^{13}$C NMR, δ 175.9, 174.7, 135.7, 133.7, 133.6, 128.9, 128.8, 128.7, 128.0, 126.5, 126.3, 125.8, 62.2, 51.9, 47.0, 42.3, 32.3, 29.4. HRMS (ESI): Mass calculated for C$_{20}$H$_{21}$N$_2$O$_2$ [M+H]: 321.1603; found: 321.1598; IR (thin film) 3282, 3004, 2922, 1692, 1605, 1585, 1498, 1455, 1424, 1400; Enantiomeric ratio was measured by chiral phase HPLC (AD-H, 10% i-PrOH/Hexanes, 1.0 mL/min, 210 nm), Rt (major)=20.75 Min, Rt (minor)=13.99 Min; e.r.=93:7.

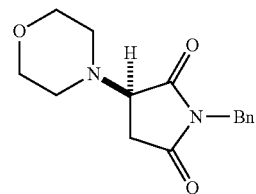 [SMILES: O=C1C[C@@H](N2CCOCC2)C(=O)N1Cc1ccccc1]

(R)-1-benzyl-3-morpholinopyrrolidine-2,5-dione (22): Prepared according to the general procedure using morpholine (0.019 g, 0.22 mmol, 1.1 equiv) to afford 0.051 g (93% yield) of product as a clear oil.

Analytical data for 22: $^1$H NMR (500 MHz, Chloroform-d) δ 7.28 (m, 5H), 4.60 (m, 2H), 3.66 (dt, J=19.5, 4.4 Hz, 5H), 2.76 (m, 3H), 2.61 (dd, J=18.4, 4.9 Hz, 1H), 2.43 (dt, J=10.3, 4.6 Hz, 2H). $^{13}$C NMR, δ 175.5, 174.5, 135.6, 128.8, 128.7, 128.0, 66.8, 62.5, 49.5, 42.2, 31.4. HRMS (ESI): Mass calculated for C$_{15}$H$_{19}$N$_2$O$_3$ [M+H]: 275.1396; found: 275.1390; IR (thin film) 2853, 1698, 1496, 1454, 1429; Enantiomeric ratio was measured by chiral phase HPLC (AD-H, 10% i-PrOH/Hexanes, 0.5 mL/min, 210 nm), Rt (major)=51.83 Min, Rt (minor)=49.28 Min; e.r.=97:3.

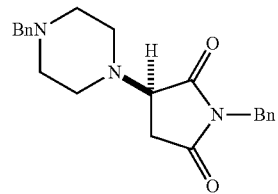 [SMILES: O=C1C[C@@H](N2CCN(Cc3ccccc3)CC2)C(=O)N1Cc1ccccc1]

(R)-1-benzyl-3-(4-benzylpiperazin-1-yl)pyrrolidine-2,5-dione (23): Prepared according to the general procedure using 1-benzylpiperazine (0.039 g, 0.22 mmol, 1.1 equiv) to afford 0.068 g (93% yield) of product as a clear oil.

Analytical data for 23: $^1$H NMR (500 MHz, Chloroform-d) δ 7.32 (m, 10H), 4.65 (d, J=5.3 Hz, 2H), 3.79 (dd, J=8.8, 4.9 Hz, 1H), 3.51 (s, 2H), 2.80 (m, 3H), 2.67 (dd, J=18.4, 5.0 Hz, 1H), 2.50 (s, 6H). $^{13}$C NMR (126 MHz, CDCl$_3$) δ 175.8, 174.7, 137.9, 135.7, 129.1, 128.8, 128.6, 128.2, 128.0, 127.1, 62.8, 62.4, 52.8, 49.0, 42.2, 31.2. Mass calculated for C$_{22}$H$_{26}$N$_3$O$_2$ [M+H]: 364; found: 364. HRMS (ESI): Mass calculated for C$_{22}$H$_{26}$N$_3$O$_2$ [M+H]: 364.2025; found: 364.2020; IR (thin film) 2918, 2814, 1692, 1496, 1453, 1426, 1401; Enantiomeric ratio was measured by chiral phase HPLC (AD-H, 10% i-PrOH/Hexanes, 1.0 mL/min, 210 nm), Rt (major)=22.91 Min, Rt (minor)=15.41 Min; e.r.=93:7.

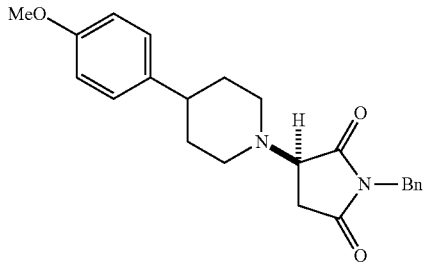 [SMILES: COc1ccc(C2CCN([C@@H]3CC(=O)N(Cc4ccccc4)C3=O)CC2)cc1]

(R)-1-benzyl-3-(4-(4-methoxyphenyl)piperidin-1-yl)pyrrolidine-2,5-dione (24): Prepared according to the general procedure using 4-(4-methoxyphenyl)piperidine (0.042 g, 0.22 mmol, 1.1 equiv) to afford 0.070 g (92% yield) of product as a colorless solid. An improved procedure was developed by only changing the temperature to −40° C. to afford 0.068 g (90% yield) of product as a colorless solid.

Analytical data for 24: $^1$H NMR (500 MHz, Chloroform-d) δ 7.33 (m, 5H), 7.12 (m, 2H), 6.84 (m, 2H), 4.67 (m, 2H), 3.85 (ddd, J=9.4, 4.8, 1.9 Hz, 1H), 3.78 (d, J=1.9 Hz, 3H), 2.87 (td, J=13.3, 11.2, 7.6 Hz, 4H), 2.69 (ddd, J=18.5, 4.9, 1.8 Hz, 1H), 2.45 (m, 1H), 2.27 (td, J=11.3, 2.7 Hz, 1H), 1.77 (m, 4H). $^{13}$C NMR (126 MHz, CDCl$_3$) δ 176.1, 174.9, 158.0, 138.0, 135.7, 128.8, 128.7, 128.0, 127.6, 113.8, 62.8, 55.2, 51.5, 48.5, 42.2, 41.4, 33.8, 33.5, 31.7. HRMS (ESI): Mass calculated for C$_{23}$H$_{27}$N$_2$O$_3$ [M+H]: 379.2022; found: 379.2016. IR (thin film) 3291, 2848, 2914, 1691, 1597, 1514, 1491, 1454, 1435.

For the standard reaction run at −20° C., enantiomeric ratio was measured by chiral phase HPLC (AD-H, 10% i-PrOH/Hexanes, 1.0 mL/min, 210 nm), Rt (major)=31.84 Min, Rt (minor)=17.77 Min; e.r.=90:10. For the same reaction run at −40° C., enantiomeric ratio was measured by chiral phase HPLC (AD-H, 10% i-PrOH/Hexanes, 1.0 mL/min, 210 nm), Rt (major)=32.26 Min, Rt (minor)=17.91 Min; e.r.=94:6.

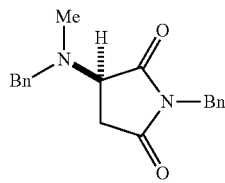 [SMILES: CN(Cc1ccccc1)[C@@H]1CC(=O)N(Cc2ccccc2)C1=O]

(R)-1-benzyl-3-(benzyl(methyl)amino)pyrrolidine-2,5-dione (25): Prepared according to the general procedure using N-methyl-phenethylamine (0.024 g, 0.22 mmol, 1.1 equiv) to afford 0.055 g (89% yield) of product as a clear oil.

Analytical data for 25: $^1$H NMR (500 MHz, Chloroform-d) δ 7.32 (m, 10H), 4.67 (m, 2H), 3.86 (m, 2H), 3.70 (d, J=13.1 Hz, 1H), 2.80 (dd, J=18.6, 9.1 Hz, 1H), 2.63 (dd, J=18.6, 4.8 Hz, 1H), 2.25 (s, 3H). $^{13}$C NMR (126 MHz, CDCl$_3$) δ 176.6, 174.9, 137.9, 135.8, 128.9, 128.8, 128.6, 128.5, 128.0, 127.5, 60.3, 59.1, 42.2, 37.2, 31.8. HRMS (ESI): Mass calculated for C$_{19}$H$_{21}$N$_2$O$_2$ [M+H]: 309.1603; found: 309.1598; IR (thin film) 3069, 2955, 1701, 1493, 1467, 1417; Enantiomeric ratio was measured by chiral phase HPLC (IA, 2% i-PrOH/Hexanes, 1.0 mL/min, 210 nm), Rt (major)=19.75 Min, Rt (minor)=20.98 Min; e.r.=78:22.

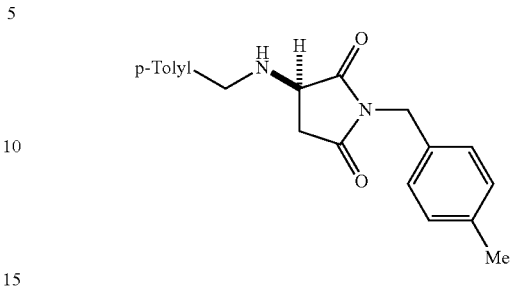

(R)-1-(4-methylbenzyl)-3-((4-methylbenzyl)amino)pyrrolidine-2,5-dione (26): Prepared according to the general procedure using 1-(4-methylbenzyl)-1H-pyrrole-2,5-dione (0.040 g, 0.20 mmol, 1.0 equiv) and p-tolylmethanamine (0.027 g, 0.22 mmol, 1.1 equiv) to afford 0.060 g (94% yield) of product as a clear solid.

Analytical data for 26: $^1$H NMR (500 MHz, Chloroform-d) δ 7.23 (s, 2H), 7.12 (m, 6H), 4.58 (d, J=2.9 Hz, 2H), 3.75 (m, 3H), 2.81 (dd, J=17.9, 8.2 Hz, 1H), 2.47 (dd, J=17.9, 5.0 Hz, 1H), 2.30 (d, J=11.1 Hz, 6H), 2.13 (s, 1H). $^{13}$C NMR (126 MHz, Chloroform-d) δ 177.7, 174.9, 137.8, 137.2, 135.6, 132.6, 129.3, 129.3, 128.8, 128.2, 55.4, 51.6, 42.2, 36.5, 21.1, 21.1. HRMS (ESI): Mass calculated for C$_{20}$H$_{23}$N$_2$O$_2$ [M+H]: 323.1760; found: 323.1554; IR (thin film) 3289, 2980, 2918, 2852, 1691, 1615, 1514, 1454, 1437; Enantiomeric ratio was measured by chiral phase HPLC (AD-H, 10% i-PrOH/Hexanes, 1.0 mL/min, 210 nm), Rt (major)=16.75 Min, Rt (minor)=13.13 Min; e.r.=92:8.

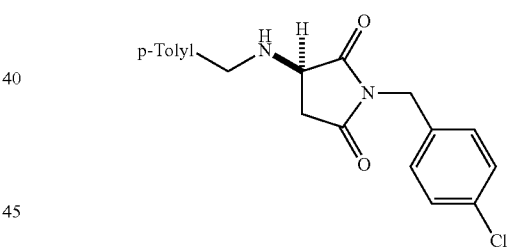

(R)-1-(4-chlorobenzyl)-3-((4-methylbenzyl)amino)pyrrolidine-2,5-dione (27): Prepared according to the general procedure using 1-(4-chlorobenzyl)-1H-pyrrole-2,5-dione (0.044 g, 0.20 mmol, 1.0 equiv) and p-tolylmethanamine (0.027 g, 0.22 mmol, 1.1 equiv) to afford 0.066 g (97% yield) of product as a clear solid.

Analytical data for 27: $^1$H NMR (500 MHz, Chloroform-d) δ 7.30 (m, 4H), 7.16 (m, 4H), 4.60 (d, J=1.9 Hz, 2H), 3.78 (m, 3H), 2.85 (dd, J=18.0, 8.2 Hz, 1H), 2.50 (dd, J=18.0, 4.9 Hz, 1H), 2.33 (s, 3H), 2.15 (s, 1H). $^{13}$C NMR (126 MHz, Chloroform-d) δ 177.5, 174.8, 137.3, 135.5, 134.0, 133.9, 130.3, 129.3, 128.8, 128.2, 55.4, 51.6, 41.7, 36.4, 21.1. HRMS (ESI): Mass calculated for C$_{19}$H$_{20}$ClN$_2$O$_2$ [M+H]: 343.1213; found: 343.1208; IR (thin film) 3291, 2917, 2847, 1691, 1597, 1514, 1491, 1454, 1435; Enantiomeric ratio was measured by chiral phase HPLC (AD-H, 10% i-PrOH/Hexanes, 1.0 mL/min, 210 nm), Rt (major)=17.92 Min, Rt (minor)=15.52 Min; e.r.=94:6.

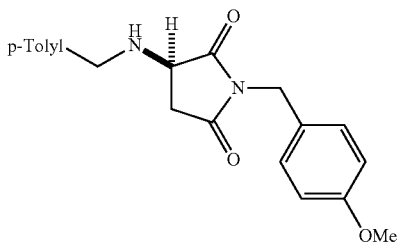

(R)-1-(4-methoxybenzyl)-3-((4-methylbenzyl)amino) pyrrolidine-2,5-dione (28): Prepared according to the general procedure using 1-(4-methoxybenzyl)-1H-pyrrole-2,5-dione (0.040 g, 0.20 mmol, 1.0 equiv) and p-tolylmethanamine (0.027 g, 0.22 mmol, 1.1 equiv) to afford 0.062 g (91% yield) of product as a clear solid.

Analytical data for 28: $^1$H NMR (500 MHz, Chloroform-d) δ 7.31 (m, 2H), 7.15 (m, 4H), 6.82 (m, 2H), 4.58 (d, J=2.8 Hz, 2H), 3.78 (m, 5H), 3.71 (dd, J=8.3, 4.9 Hz, 1H), 2.83 (dd, J=17.9, 8.3 Hz, 1H), 2.48 (dd, J=17.9, 5.0 Hz, 1H), 2.33 (s, 3H), 2.15 (s, 1H). $^{13}$C NMR (126 MHz, Chloroform-d) δ 177.7, 174.9, 159.3, 137.2, 135.6, 130.3, 129.3, 128.2, 127.8, 114.0, 55.4, 55.3, 51.6, 41.9, 36.4, 21.1. HRMS (ESI): Mass calculated for $C_{20}H_{23}N_2O_3$ [M+H]: 339.1709; found: 339.1703; IR (thin film): 3284, 3018, 2913, 2857, 1687, 1614, 1585, 1513, 1437, 1398, 1353; Enantiomeric ratio was measured by chiral phase HPLC (AD-H, 10% i-PrOH/Hexanes, 1.0 mL/min, 210 nm), Rt (major)=31.8 Min, Rt (minor)=23.20 Min; e.r.=87:13.

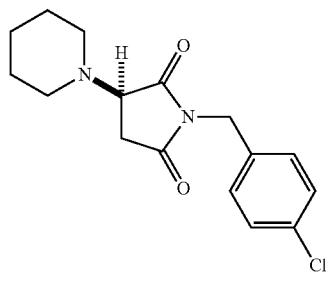

(R)-1-(4-chlorobenzyl)-3-(piperidin-1-yl)pyrrolidine-2,5-dione (29): Prepared according to the general procedure using 1-(4-chlorobenzyl)-1H-pyrrole-2,5-dione (0.044 g, 0.20 mmol, 1.0 equiv) and piperidine (0.019 g, 0.22, 1.1 equiv) to afford 0.055 g (89% yield) of product as a clear solid.

Analytical data for 29: $^1$H NMR (500 MHz, Chloroform-d) δ 7.30 (m, 4H), 4.62 (m, 2H), 3.77 (dd, J=9.1, 4.7 Hz, 1H), 2.82 (dd, J=18.6, 9.0 Hz, 1H), 2.67 (m, 3H), 2.40 (dt, J=10.8, 5.3 Hz, 2H), 1.55 (d, J=5.5 Hz, 4H), 1.44 (m, 2H). $^{13}$C NMR (126 MHz, Chloroform-d) δ 176.1, 174.9, 134.2, 133.9, 130.3, 128.8, 63.2, 50.2, 41.4, 31.6, 26.0, 24.0. HRMS (ESI): Mass calculated for $C_{16}H_{20}ClN_2O_2$ [M+H]: 307.1213; found: 323.1208; IR (thin film) 2927, 2822, 1688, 1508, 1449, 1424, 1395. For the standard reaction run at −20° C., enantiomeric ratio was measured by chiral phase HPLC (AD-H, 10% i-PrOH/Hexanes, 1.0 mL/min, 210 nm), Rt (major)=10.68 Min, Rt (minor)=13.16 Min; e.r.=93:7. For the same reaction run at −40° C., enantiomeric ratio was measured by chiral phase HPLC (AD-H, 10% i-PrOH/Hexanes, 1.0 mL/min, 210 nm), Rt (major)=10.64 Min, Rt (minor)=13.13 Min; e.r.=84:16.

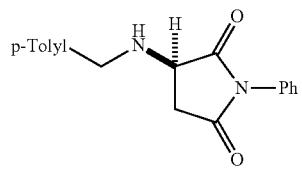

(R)-3-((4-methylbenzyl)amino)-1-phenylpyrrolidine-2,5-dione (30): Prepared according to the general procedure using p-tolylmethanamine (0.027 g, 0.22 mmol, 1.1 equiv) and 1-phenyl-1H-pyrrole-2,5-dione (0.035 g, 0.2 mmol, 1.0 equiv) to afford 0.059 g (93% yield) of 30 as a white solid.

Analytical data for 30: $^1$H NMR (500 MHz, Chloroform-d) δ 7.50 (dd, J=8.4, 7.0 Hz, 2H), 7.43 (m, 1H), 7.29 (m, 4H), 7.20 (d, J=7.7 Hz, 2H), 3.95 (m, 3H), 3.05 (dd, J=18.0, 8.4 Hz, 1H), 2.73 (dd, J=18.0, 5.3 Hz, 1H), 2.38 (s, 4H). $^{13}$C NMR (126 MHz, CDCl$_3$) δ 176.8, 174.1, 137.4, 135.3, 131.6, 129.4, 129.2, 128.7, 128.4, 126.3, 55.4, 51.6, 36.5, 21.1. HRMS (ESI): Mass calculated for $C_{18}N_{19}N_2O_2$ [M+H]: 295.1447; found: 295.1441; IR (thin film): 3299, 3047, 1698, 1594, 1513, 1495, 1453, 1395, 1370. Enantiomeric ratio was measured by chiral phase HPLC (IA, 30% i-PrOH/Hexanes, 0.5 mL/min, 210 nm), Rt (major)=28.33 Min, Rt (minor)=27.03 Min; e.r.=74:26.

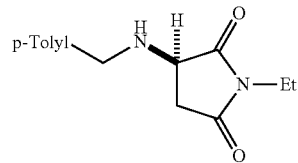

(R)-1-ethyl-3-((4-methylbenzyl)amino)pyrrolidine-2,5-dione (31): Prepared according to the general procedure using p-tolylmethanamine (0.027 g, 0.22 mmol, 1.1 equiv) and 1-ethyl-1H-pyrrole-2,5-dione (0.025 g, 0.20 mmol, 1.0 equiv) to afford 0.045 g (91% yield) of product 31 as a clear oil.

Analytical data for 31: $^1$H NMR (500 MHz, Chloroform-d) δ 7.17 (m, 4H), 3.81 (m, 2H), 3.72 (dd, J=8.2, 4.9 Hz, 1H), 3.55 (q, J=7.2 Hz, 2H), 2.83 (dd, J=17.9, 8.2 Hz, 1H), 2.49 (dd, J=17.9, 4.9 Hz, 1H), 2.34 (s, 3H), 1.16 (t, J=7.2 Hz, 3H). $^{13}$C NMR (126 MHz, CDCl$_3$) δ 177.8, 175.2, 137.3, 135.5, 129.3, 128.2, 55.4, 51.7, 36.5, 33.8, 21.1, 13.0. HRMS (ESI): Mass calculated for $C_{14}H_{19}N_2O_2$ [M+H]: 247.1447; found: 247.1441; IR (thin film) 3294, 2981, 2848, 1686, 1516, 1491, 1447, 1405; Enantiomeric ratio was measured by chiral phase HPLC (AD-H, 10% i-PrOH/Hexanes, 1.0 mL/min, 210 nm), Rt (major)=12.56 Min, Rt (minor)=11.21 Min; e.r.=80:20.

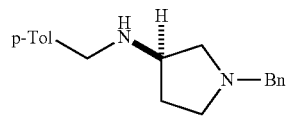

(R)-1-benzyl-N-(4-methylbenzyl)pyrrolidin-3-amine (34): A flame-dried 25 mL round bottom flask equipped with a magnetic stirring bar and a nitrogen inlet was charged with THF (7.6 mL) and lithium aluminum hydride (0.215 g, 5.67 mmol, 5.0 equiv). To the resulting suspension was added 1-benzyl-3-((4-methylbenzyl)amino)pyrrolidine-2,5-dione 6 (0.350 g, 1.135 mmol) portion-wise as a solid. The reaction flask was equipped with a reflux condenser and heated to 60° C. for 14 h. The reaction mixture was then cooled to 23° C. and poured into ice cold 1.0 M NaOH (50 mL) and stirred for 10 min. The mixture was transferred to a separatory funnel and extracted with diethyl ether (3×100 mL). The organic layer was collected, dried over sodium sulfate, filtered and concentrated on a rotary evaporator to give the product 34 as analytically pure pale yellow oil (0.305 g, 1.08 mmol, 95%).

Analytical data for 34: $^1$H NMR (500 MHz, Chloroform-d) δ 7.31 (dt, J=8.6, 4.1 Hz, 4H), 7.25 (m, 2H), 7.19 (m, 2H), 7.11 (m, 2H), 3.69 (d, J=1.8 Hz, 2H), 3.60 (qd, J=12.9, 1.8 Hz, 2H), 3.34 (ddtd, J=8.8, 6.7, 4.8, 1.7 Hz, 1H), 2.75 (ddd, J=8.8, 6.7, 1.7 Hz, 1H), 2.63 (tdd, J=8.4, 6.0, 1.8 Hz, 1H), 2.53 (tdd, J=9.4, 6.7, 1.7 Hz, 1H), 2.39 (ddd, J=9.5, 5.0, 1.8 Hz, 1H), 2.33 (d, J=1.7 Hz, 3H), 2.13 (m, 1H), 1.61 (dddt, J=12.8, 10.9, 6.1, 3.0 Hz, 1H), 1.37 (s, 1H). $^{13}$C NMR (126 MHz, CDCl$_3$) δ 139.1, 137.3, 136.4, 129.0, 128.8, 128.2, 128.1, 126.9, 60.8, 60.5, 56.7, 53.1, 52.1, 32.2, 21.1. HRMS (ESI): Mass calculated for $C_{19}H_{25}N_2$ [M+H]: 281.2018; found: 281.2012; IR (thin film): 3025, 2955, 2910, 2783, 1514, 1494, 1452; Enantiomeric ratio was measured by chiral phase HPLC (OD-H, 5% i-PrOH/Hexanes, 1.0 mL/min, 210 nm), Rt (major)=15.91 Min, Rt (minor)=11.56 Min; e.r.=99:1.

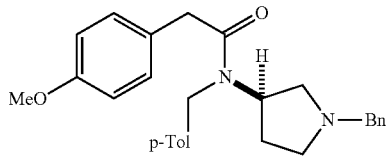

(R)—N-(1-benzylpyrrolidin-3-yl)-2-(4-methoxyphenyl)-N-(4-methylbenzyl)acetamide (35): To a 25 ml flask charged with dichloromethane (10.9 ml) was added sequentially (R)-1-benzyl-N-(4-methylbenzyl)pyrrolidin-3-amine 34 (0.305 g, 1.088 mmol), Hunig's Base (2.280 mL, 13.05 mmol, 12 equiv), and 2-(4-methoxyphenyl)acetyl chloride (0.602 g, 3.26 mmol, 3.0 equiv) at 23° C. The reaction was allowed to stir at 23° C. for 48 h, at which point it was poured into a separatory funnel containing saturated NaHCO$_3$(10 mL) and extracted with dichloromethane (3×15 mL). The combined organic layers were washed with water (15 mL), saturated brine (15 mL), then dried over Na$_2$SO$_4$, filtered, and concentrated on a rotary evaporator. The crude residue was purified via column chromatography (9:1 hexanes:acetone) to afford product 35 as a colorless oil (0.201 g, 0.469 mmol, 43%), which was characterized as a ~2:1 mixture of amide rotamers at 23° C. by NMR.

Analytical data for 35: $^1$H NMR (500 MHz, Chloroform-d) δ 7.20 (m, 11H), 7.06 (q, J=8.5, 7.4 Hz, 6H), 6.83 (dd, J=20.1, 8.1 Hz, 3H), 5.17 (m, 1H), 4.65 (dt, J=32.4, 18.0 Hz, 4H), 3.79 (d, J=7.3 Hz, 6H), 3.54 (t, J=14.2 Hz, 2H), 3.47 (m, 4H), 2.79 (t, J=7.5 Hz, 1H), 2.59 (ddd, J=26.5, 10.4, 4.0 Hz, 1H), 2.47 (t, J=9.1 Hz, 1H), 2.30 (m, 8H), 1.90 (t, J=8.8 Hz, 1H), 1.70 (dt, J=18.2, 6.2 Hz, 2H). $^{13}$C NMR (126 MHz, CDCl$_3$) δ 172.4, 171.4, 158.4, 138.9, 138.5, 136.7, 136.6, 136.0, 135.7, 129.7, 129.7, 129.5, 129.0, 128.6, 128.4, 128.3, 128.2, 127.3, 127.1, 127.0, 126.8, 126.8, 125.4, 114.1, 114.0, 60.0, 57.5, 57.4, 57.0, 56.0, 55.2, 53.6, 53.3, 53.3, 47.5, 45.5, 40.9, 40.6, 30.0, 29.9, 24.7, 21.0. HRMS (ESI): Mass calculated for $C_{28}H_{33}N_2O_2$ [M+H]: 429.2542; found: 429.2537; IR (thin film): 3334, 3055, 2898, 2875, 1716, 1652, 1558, 1512, 1456, 1419, 1379.

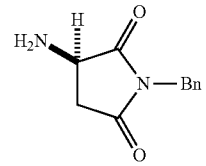

(R)-3-amino-1-benzylpyrrolidine-2,5-dione (36): To a flame dried 10 mL round bottom flask under an inert atmosphere was added 10% Pd/C (21.28 mg, 0.020 mmol), (R)-1-benzyl-3-((4-methylbenzyl)amino)pyrrolidine-2,5-dione 6 (61.7 mg, 0.2 mmol), followed by MeOH (4.0 ml). The flask was then equipped with a balloon of H$_2$ (1 atm) and stirred at 23° C. for 5 h, at which point the reaction mixture was filtered through a 0.5 cm plug of Celite™. The filter cake was rinsed with 20 mL of ethyl acetate, and the resulting clear homogeneous filtrate was concentrated in vacuo. The resulting crude residue was purified on SiO$_2$ in the following manner: a chloroform solution (0.5 mL) of the crude residue was loaded onto a dry pad of silica gel (2×2 cm), which was first flushed with hexanes (15 mL) then with MeCN (~15 mL) until all of 36 had been eluted (TLC monitoring). The MeCN eluent was concentrated in vacuo to give 36 as a colorless solid (39 mg, 0.192 mmol, 96% yield).

Analytical data for 36: $^1$H NMR (500 MHz, Chloroform-d) δ 7.34 (m, 5H), 4.66 (s, 2H), 3.90 (dd, J=8.7, 5.3 Hz, 1H), 3.05 (dd, J=18.1, 8.7 Hz, 1H), 2.46 (dd, J=18.1, 5.4 Hz, 1H) 1.68 (s, 2H). $^{13}$C NMR (126 MHz, CDCl$_3$) δ 179.0, 174.5, 135.5, 128.9, 128.7, 128.1, 50.5, 42.5, 37.9. HRMS (ESI): Mass calculated for $C_{11}H_{13}N_2O_2$ [M+H]: 205.0977; found: 205.0972; IR (thin film): 3302, 3036, 2932, 2810, 1697, 1608, 1581, 1512, 1501, 1455, 1423, 1362. Enantiomeric ratio was measured by chiral phase HPLC (OD-H, 2% i-PrOH/Hexanes, 1.0 mL/min, 210 nm), Rt (major)=52.71 Min, Rt (minor)=not observed Min; e.r.=>99:1.

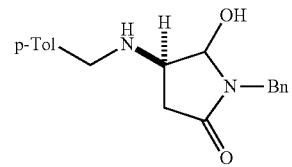

(R)-1-benzyl-4-((4-methylbenzyl)amino)-5-hydroxypyrrolidin-2-one (SI-1): To a flame dried 25 mL flask charged with 2:1 CH$_2$Cl$_2$:MeOH (2 mL) was added (R)-1-benzyl-3-((4-methylbenzyl)amino)pyrrolidine-2,5-dione 6 (61.7 mg, 0.2 mmol), and the resulting solution was cooled to 0° C. using an external ice bath. Sodium borohydride (7.6 mg, 0.2 mmol, 1.0 equiv) was added in a single bolus, after which the reaction was warmed to 4° C. and stirred at this temperature for 14 h. The crude reaction was quenched with 5 mL saturated aqueous NaHCO$_3$, washed into a separatory funnel with 5 mL of EtOAc, and extracted with EtOAc (3×5 mL). The combined organic layers were washed with saturated aqueous brine (5 mL), dried over Na$_2$SO$_4$, filtered and concentrated on a rotary evaporator. The crude oily product was triturated with ethyl acetate, resulting in precipitation of a white solid. The precipitate was filtered, washed with cold ethyl acetate (0.5 mL) and dried under high-vacuum (~0.1

Torr) to give a white solid (0.026 g, 0.084 mmol, 42%) which was characterized as the trans-isomer of SI-1.

Analytical data for trans-SI-1: $^1$H NMR (500 MHz, Chloroform-d) δ 7.32 (m, 6H), 7.13 (m, 4H), 4.83 (m, 2H), 4.25 (d, J=14.9 Hz, 1H), 3.72 (m, 2H), 3.23 (m, 1H), 2.85 (dd, J=17.1, 7.6 Hz, 1H), 2.33 (s, 3H), 2.22 (dd, J=17.2, 4.1 Hz, 1H), 2.07 (s, 1H). $^{13}$C NMR (126 MHz, CDCl$_3$), δ 172.6, 137.0, 136.3, 136.2, 129.2, 128.8, 128.3, 128.1, 127.7, 87.7, 59.7, 51.5, 43.6, 37.1, 21.1.

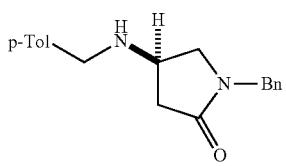

(R)-1-benzyl-4-((4-methylbenzyl)amino)pyrrolidin-2-one (37): To a 25 mL round bottom flask was added SI-1 (49 mg, 0.158 mmol, 1.0 equiv), followed by dichloromethane (16 mL), and triethylsilane (0.252 mL, 1.58 mmol, 10.0 equiv). The resulting solution was cooled to −78° C. in an acetone/dry ice bath, whereupon BF$_3$·OEt$_2$ (0.050 mL, 0.395 mmol, 2.5 equiv) was added dropwise via syringe. The cooling bath was removed after 15 min, and the reaction was stirred at 23° C. for 16 h. The crude reaction was quenched by addition of 10 mL of saturated aqueous NaHCO$_3$, and then transferred to a separatory funnel. The mixture was extracted with dichloromethane (3×15 mL), and the combined organic portions were washed with brine (15 mL), collected and dried over sodium sulfate, filtered, and concentrated to a crude oily residue. The crude product was purified via flash column chromatography (Hexanes:Acetone, gradient 10:1→1:1) to yield 37 as a colorless oil (39 mg, 0.132 mmol, 84%).

Analytical data for 37: $^1$H NMR (500 MHz, Chloroform-d) δ 7.31 (m, 4H), 7.24 (m, 2H), 7.12 (m, 4H), 4.46 (d, J=2.9 Hz, 2H), 3.69 (m, 2H), 3.48 (tt, J=7.5, 5.0 Hz, 1H), 3.42 (dd, J=9.8, 6.9 Hz, 1H), 3.07 (dd, J=9.8, 4.4 Hz, 1H), 2.69 (dd, J=16.9, 7.7 Hz, 1H), 2.34 (m, 4H). $^{13}$C NMR (126 MHz, CDCl$_3$), δ 173.0, 136.9, 136.4, 136.3, 129.2, 128.7, 128.1, 128.0, 127.6, 53.0, 51.4, 50.3, 46.4, 38.9, 21.1. HRMS (ESI): Mass calculated for C$_{19}$H$_{23}$N$_2$O [M+H]: 295.1810; found: 295.1805; IR (thin film): 3283, 3017, 2919, 2856, 1685, 1614, 1585, 1513, 1496, 1437, 1399, 1354. Enantiomeric ratio was measured by chiral phase HPLC (AD-H, 10% i-PrOH/Hexanes, 1.0 mL/min, 210 nm), Rt (major) =18.35 Min, Rt (minor)=20.53 Min; e.r.=97:3.

REFERENCES

[1] Pangborn, A. B.; Giardello, M. A.; Grubbs, R. H.; Rosen, R. K.; Timmers F. J., *Organometallics* 1996, 15, 1518-1520.
[2] Perrin, D. D.; Armarego, W. L. *Purification of Laboratory Chemicals;* 3rd Ed., Pergamon Press, Oxford. 1988.
[3] Isozaki, H.; Yasugi, M.; Takigawa, N.; Hotta, K.; Ichihara, E.; Taniguchi, A.; Toyooka, S.; Hashida, S.; Sendo, T.; Tanimoto, M.; Kiura, K.; *Jpn. J. Clin. Onc.* 2014, 44, 963-968.
[4] Katayama, R.; Khan, T. M.; Benes, C.; Lifshits, E.; Ebi, H.; Rivera, W. M.; Shakespeare, W. C.; Iafrate, A. J.; Engelmana, J. A.; Shaw, A. T., *Proc. Nat. Acad. Sci. U.S.A.* 2011, 108, 7535.
[5] Katayama R.; Shaw A. T.; Khan T. M.; Mino-Kenudson, M.; Solomon, B. J.; Halmos, B.; Jessop, N. A.; Wain, J. C.; Yeo, A. T.; Benes, C.; Drew, L.; Saeh, IC.; Crosby, K.; Sequist, L. V.; Iafrate, A. J; Engelman, J. A., *Sci. Trans, Med.* 2012, 4, 120.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A compound of a formula:

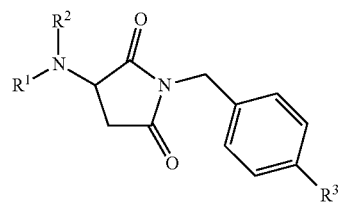

wherein
R$^1$ is selected from the group consisting of alkyl, cycloalkyl, alkenyl, and —CH$_2$—R$^{1'}$,
wherein R$^{1'}$ is selected from the group consisting of aryl, arylalkyl, and cycloalkyl, and
R$^{1'}$ is optionally substituted at one or more positions with alkyl, halo, or alkoxy;
R$^2$ is hydrogen or alkyl; and
R$^3$ is hydrogen, alkyl, alkoxy, or halo.

2. The compound of claim 1 of a formula:

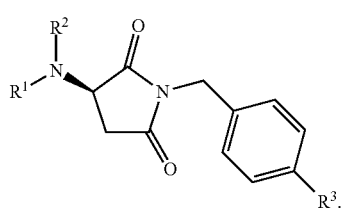

3. The compound of claim 1, wherein $R^1$ is $C_1$-$C_{12}$ alkyl, $C_3$-$C_8$ cycloalkyl, or $C_2$-$C_{12}$ alkenyl.

4. The compound of claim 1, wherein $R^1$ has a formula —$CH_2$—$R^{1'}$, and $R^{1'}$ is phenyl, benzyl, or $C_3$-$C_8$ cycloalkyl, which optionally is substituted at one or more positions with alkyl, halo, or alkoxy.

5. The compound of claim 1, wherein $R^2$ is hydrogen or methyl.

6. The compound of claim 1, wherein $R^3$ is hydrogen, methyl, methoxy, or chloro.

7. The compound of claim 1, selected from the group consisting of

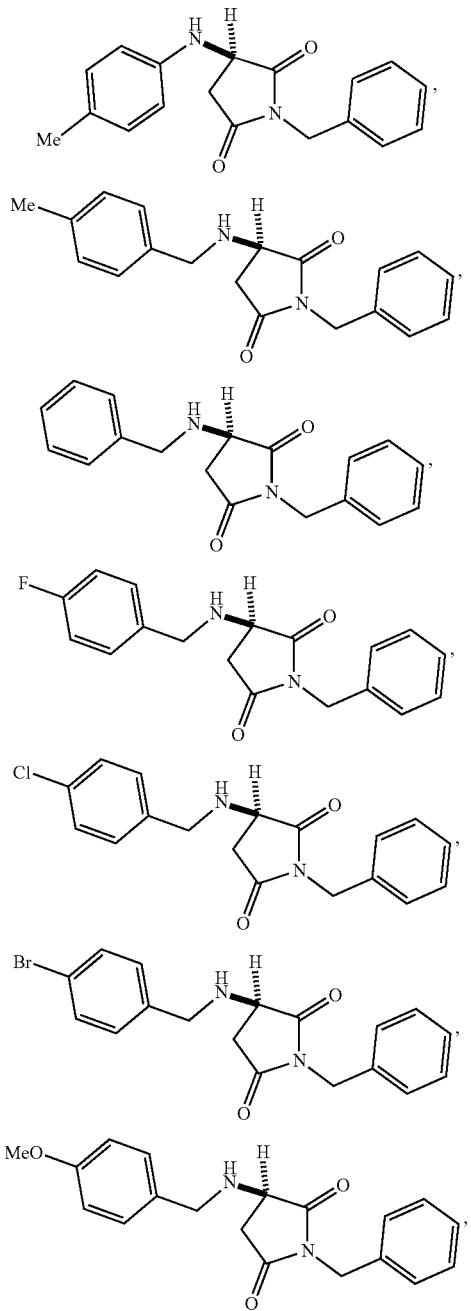

-continued

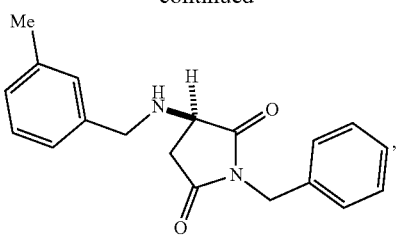

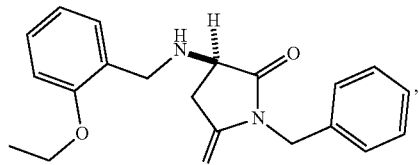

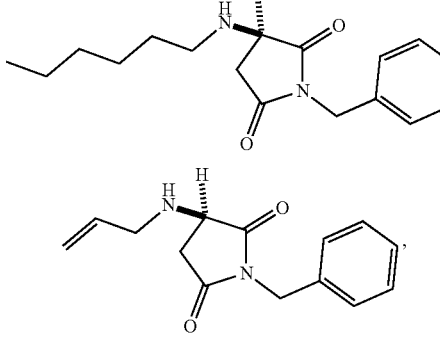

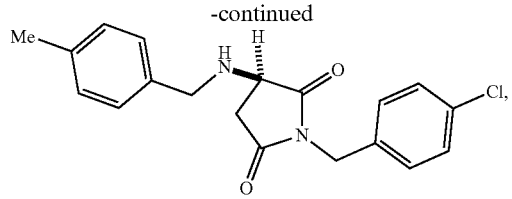
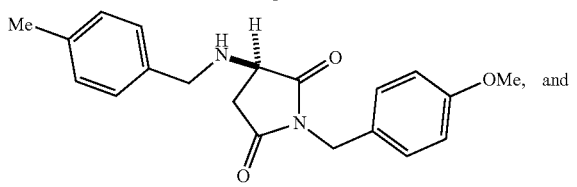
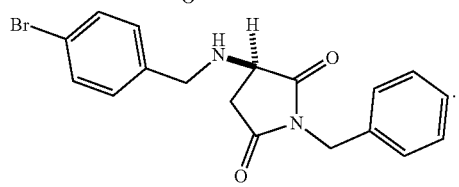
* * * * *